(12) United States Patent
Krause et al.

(10) Patent No.: US 11,542,524 B2
(45) Date of Patent: *Jan. 3, 2023

(54) ELIMINATION OF PROLIFERATING CELLS FROM STEM CELL-DERIVED GRAFTS

(71) Applicant: Research Development Foundation, Carson City, NV (US)

(72) Inventors: Karl-Heinz Krause, Geneva (CH); Michel Dubois-Dauphin, Geneva (CH); Vannary Tieng Caulet, Geneva (CH)

(73) Assignee: Research Development Foundation, Carson City, NV (US)

( * ) Notice: Subject to any disclaimer, the term of this patent is extended or adjusted under 35 U.S.C. 154(b) by 980 days.

This patent is subject to a terminal disclaimer.

(21) Appl. No.: 16/204,320

(22) Filed: Nov. 29, 2018

(65) Prior Publication Data

US 2019/0160113 A1 May 30, 2019

Related U.S. Application Data

(60) Provisional application No. 62/592,219, filed on Nov. 29, 2017.

(51) Int. Cl.

| | | |
|---|---|---|
| *C12N 15/86* | (2006.01) | |
| *A61K 35/545* | (2015.01) | |
| *A61K 31/522* | (2006.01) | |
| *C12N 5/079* | (2010.01) | |
| *C12N 9/12* | (2006.01) | |
| *A61K 35/12* | (2015.01) | |
| *A61K 9/00* | (2006.01) | |

(52) U.S. Cl.
CPC ............ *C12N 15/86* (2013.01); *A61K 31/522* (2013.01); *A61K 35/12* (2013.01); *A61K 35/545* (2013.01); *C12N 5/0618* (2013.01); *C12N 9/1211* (2013.01); *A61K 9/0019* (2013.01); *C12N 2501/10* (2013.01); *C12N 2501/11* (2013.01); *C12N 2506/02* (2013.01); *C12N 2506/45* (2013.01); *C12N 2740/15043* (2013.01); *C12N 2740/16043* (2013.01); *C12N 2830/007* (2013.01)

(58) Field of Classification Search
None
See application file for complete search history.

(56) References Cited

U.S. PATENT DOCUMENTS

| | | |
|---|---|---|
| 5,585,096 A | 12/1996 | Martuza et al. |
| 5,631,236 A | 5/1997 | Woo et al. |
| 5,691,177 A | 11/1997 | Gruber et al. |
| 5,877,010 A | 3/1999 | Loeb et al. |
| 5,985,266 A | 11/1999 | Link et al. |
| 6,451,571 B1 | 9/2002 | Loeb et al. |
| 6,528,245 B2 | 3/2003 | Sanchez-Ramos et al. |
| 2004/0151697 A1 | 8/2004 | Martuza et al. |
| 2006/0216312 A1 | 9/2006 | Jacobs |
| 2009/0298156 A1* | 12/2009 | Black ...................... A61P 11/00 435/194 |
| 2012/0117668 A1 | 5/2012 | Fleischmann et al. |
| 2012/0142071 A1 | 6/2012 | Black |
| 2012/0149890 A1 | 6/2012 | Black |
| 2013/0011903 A1 | 1/2013 | Black |
| 2014/0057969 A1 | 2/2014 | Frost et al. |
| 2015/0299278 A1 | 10/2015 | Orrichio et al. |

FOREIGN PATENT DOCUMENTS

| | | | |
|---|---|---|---|
| CN | 101319215 | 12/2008 | |
| JP | 2006-345726 | 12/2006 | |
| WO | WO 1991/002805 | 3/1991 | |
| WO | WO 2011-006962 | 1/2011 | |
| WO | WO 2011/010965 | 1/2011 | |
| WO | WO 2011/109837 | 12/2011 | |
| WO | WO-2018005975 A1 * | 1/2018 | ............ A61K 35/30 |

OTHER PUBLICATIONS

Andrei et al., "Characterization of Herpes Simplex Virus Type 1 Thymidine Kinase Mutants Selected under a Single Round of High-Dose Brivudin," *J. Virol.*, 79: 5863-5869, 2005.

Black et al., "Creation of drug-specific herpes simplex virus type 1 thymidine kinase mutants for gene therapy," *Proc. Natl. Acad. U.S.A.*, 93:3525-3529, 1996.

Black et al., "Herpes simplex virus-1 thymidine kinase mutants created by semi-random sequence mutagenesis improve prodrug-mediated tumor cell killing," *Cancer Res.*, 61(7):3022-6, 2001.

Cao et al., "Molecular Imaging of Embryonic Stem Cell Misbehavior and Suicide Gene Ablation," *Cloning and Stem Cells*, 9(1):107-117, 2007.

Chalmers et al., "Elimination of the Truncated Message from the Herpes Simplex Virus Thymidine Kinase Suicide Gene," *Mol Ther.*, 4:146-148, 2001.

Chen et al., "Suicide gene-mediated ablation of tumor-initiating mouse pluripotent stem cells," *Biomaterials*, 34(6):1701-1711, 2013.

Chou et al., "Differentiated Levels of Ganciclovir Resistance Conferred by Mutations at Codons 591 to 603 of the Cytomegalovirus UL97 Kinase Gene," *Journal of Clinical Microbiology*, 55(7):2098-2104, 2017.

Denny, "Prodrugs for Gene-Directed Enzyme-Prodrug Therapy (Suicide Gene Therapy)," *J. Biomed. Biotechnol.*, 1:48-70, 2003.

Dimova et al., "The E2F transcriptional network: old acquaintances with new faces," *Oncogene*, 24:2810-2826, 2005.

(Continued)

*Primary Examiner* — Marcia S Noble
(74) *Attorney, Agent, or Firm* — Parker Highlander PLLC

(57) ABSTRACT

Provided herein are methods and compositions for a suicide gene approach comprising an expression vector comprising a cell cycle-dependent promoter driving the expression of a suicide gene. Also provided herein are methods to render proliferative cells sensitive to a prodrug after transplantation but avoids expression of the suicide gene in post-mitotic cells, such as neurons.

16 Claims, 10 Drawing Sheets
(10 of 10 Drawing Sheet(s) Filed in Color)
Specification includes a Sequence Listing.

(56) References Cited

OTHER PUBLICATIONS

Fischer et al., "The p53-p21-DREAM-CDE/CHR pathway regulates G2/M cell cycle genes," *Nucleic Acids Res.*, 44(1):164-174, 2016.
Ganat et al., "Identification of embryonic stem cell-derived midbrain dopaminergic neurons for engraftment," *J. Clin. Invest.*, 122:2928-2939, 2012.
Gargett et al., "The inducible caspase-9 suicide gene system as a "safety switch" to limit on-target, off-tumor toxicities of chimeric antigen receptor T cells," *Front. Pharmacol.*, 5:235, 2014.
Hara et al., "Neuron-like differentiation and selective ablation of undifferentiated embryonic stem cells containing suicide gene with Oct-4 promoter," *Stem Cells Dev.*, 17:619-628, 2008.
Hoffman et al., "Efficient generation of double heterologous promoter controlled oncolytic adenovirus vectors by a single homologous recombination step in Escherichia coli," *BMC Biotechnol.*, 6(36):1-12, 2006.
Imaki et al., "Cell cycle-dependent regulation of the Skp2 promoter by GA-binding protein," *Cancer Res.*, 63(15):4607-13, 2003.
Jung et al., "Ablation of Tumor-derived stem cells transplanted to the central nervous system by genetic modification by embryonic stem cells with a suicide gene," *Human Gene Ther.*, 18:1182-1192, 2007.
Kang et al., "Cyclin A regulates a cell-cycle-dependent expression of CKAP2 through phosphorylation of Sp1," *Biochem. Biophys. Res. Commun.*, 420(4):822-7, 2012.
Knoepfler, "Deconstructing Stem Cell Tumorigenicity: A Roadmap to Safe Regenerate Medicine," *Stem Cells*, 27:1050-1056, 2009.
Kotini et al., "Escape Mutations, Ganciclovir Resistance, and Teratoma Formation in Human iPSCs Expressing an HSVtk Suicide Gene," *Mol. Ther. Nucleic Acids*, 5:e284, 2016.
Kriks et al., "Floor plate-derived dopemine neurons from hESCs efficiently engraft in animal models of PD," *Nature*, 480:547-551, 2011.
Li and Xiang, "Safeguarding clinical translation of pluripotent stem cells with suicide genes," *Organogenesis*, 9(1):34-39, 2013.
Malecki, "'Above all, do no harm': safeguarding pluripotent stem cell therapy against iatrogenic tumorigenesis," *Stem Cell Res. Ther.*, 5(73):1-10, 2014.
McKnight et al. "The nucleotide sequence and transcript map of the herpes simplex virus thymidine kinase gene," *Nucl. Acids Res.* 8(24):5949-5964, 1980.
Muller et al., "The CHR promoter element controls cell cycle-dependent gene transcription and binds the DREAM and MMB complexes," *Nucleic Acids Res.* 40(4):1561-1578, 2012.
Naujok et al., "Selective removal of undifferentiated embryonic stem cells from differentiation cultures through HSV1 thymidine kinase and ganciclovir treatment," *Stem Cell Rev.*, 6(3):450-61, 2010.
PCT International Search Report and Written Opinion issued in International Application No. PCT/US2017/040303, dated Oct. 27, 2017.
PCT International Search Report and Written Opinion issued in International Application No. PCT/US2018/063035, dated Feb. 5, 2019.
Qasim et al., "T cell transduction and suicide with an enhanced mutant thymidine kinase," *Gene Therapy*, 9:824-827, 2002.
Ren et al., "E2F integrates cell cycle progression with DNA repair, replication, and G(2)/M checkpoints," *Genes Dev.* 16(2):245-256, 2002.
Rong et al., "A Scalable Approach to Prevent Teratoma Formation of Human Embryonic Stem Cells," *J. Biol. Chem.*, 287(39):32338-32345, 2012.
Salvatore et al., "A Cell Proliferation and Chromosomal Instability Signature in Anaplastic Thyroid Carcinoma," *Cancer Res.* 67(21):10148-10158, 2007.
Schuldiner et al., "Selective ablation of human embryonic stem cells expressing a "suicide" gene," *Stem Cells*, 21:257-265, 2003.
Straathof et al., "Suicide genes as safety switches in T lymphocytes," *Cytotherapy*, 5(3):227-230, 2003.
Sundaram et al., "A new nucleoside analogue with potent activity against mutant sr39 herpes simplex virus-1 (HSV-1) thymidine kinase (TK)," *Org. Lett.*, 14(14):3568-3571, 2012.
Tey, "Adoptive T-cell therapy: adverse events and safety switches," *Clin. Transl. Immunol.*, 3(6):e17, 2014.
Tieng et al., "Elimination of proliferating cells from CNS grafts using a Ki67 promoter-driven thymidine kinase," *Molecular Therapy— Methods & Clinical Development*, 6:16069, 2016.
Wernig et al., "Neurons derived from reprogrammed fibroblasts functionally integrate into the fetal brain and improve symptoms of rats with Parkinson's disease," *Proc. Natl. Acad. Sci. U.S.A.*, 105:5856-5861, 2008.
Wu et al., "Development of an inducible caspase-9 safety switch for pluripotent stem cell-based therapies," *Mol. Ther. Methods Clin. Dev.*, 1(14053):1-11, 2014.
Wu et al., "Human Dbf4/ASK promoter is activated through the Sp1 and MluI cell-cycle box (MCB) transcription elements," *Oncogene*, 21(51): 7786-96, 2002.
Zambon, "Use of the Ki67 Promoter to Label Cell Cycle Entry in Living Cells," *Cytometry A.*, 77(6):564-570, 2010.
Amariglio et al., "Donor-derived brain tumor following neural stem cell transplantation in an ataxia telangiectasia patient," *PLoS Medicine*, 6(2):e1000029, 2009.
Andressen et al., "Nestin-specific green fluorescent protein expression in embryonic stem cell-derived neural precursor cells used for transplantation," 19:419-424, 2001.
Anisimov et al., "Risks and mechanisms of oncological disease following stem cell transplantation," *Stem Cell Reviews and Reports*, 6(3):411-424, 2010.
Dihne et al., "Embryonic stem cell-derived neuronally committed precursor cells with reduced teratoma formation after transplantation into the lesioned adult mouse brain," 24:1458-1466, 2006.
Extended European Search Report issued in European Application No. 17821362.5, dated Dec. 13, 2019.
Gunaseeli et al., "Induced pluripotent stem cells as a model for accelerated patient- and disease-specific drug discovery," *Curr Med Chem.*, 17(8):759-766, 2010.
Hardwick and Philpott, "Nervous decision-making: to divide or differentiate," *Trends in Genetics*, 30(6):254-261, 2014.
Johnson et al., "Expression of transcription factor E2F1 induces quiescent cells to enter S phase," *Nature*, 365:349-352, 1993.
Kanazawa et al., "Suicide gene therapy using AAV-HSVtk/ganciclovir in combination with irradiation results in regression of human head and neck cancer xenografts in nude mice," *Gene Therapy*, 10:51-58, 2003.
Kawamura et al., "Transcriptional regulatory regions of the survivin gene activate an exogenous suicide gene in human tumors and enhance the sensitivity to a prodrug," *Anticancer Research*, 27:89-94, 2007.
Lim et al., "Lentiviral vector mediated thymidine kinase expression in pluripotent stem cells enables removal of tumorigenic cells," *PLoS ONE*, 8(7):e70543, 2013.
Malecki et al., "Safeguarding stem cell-based regenerative therapy against iatrogenic cancerogenesis," *J Stem Cell Res Ther.*, Suppl 9(5):21559, 2013.
Morgan, "Live and let die: a new suicide gene therapy moves to the clinic," *Molecular Therapy*, 20(1):11-13, 2012.
Office Action issued in European Application No. 17821362.5, dated Aug. 18, 2021.
Office Action issued in Japanese Application No. 2018-567868, dated Jul. 13, 2021, and English summary.
Office Action issued in U.S. Appl. No. 15/639,765, dated Aug. 27, 2021.
Office Action issued in U.S. Appl. No. 15/639,765, dated Apr. 26, 2022.
Office Action issued in U.S. Appl. No. 15/639,765, dated Dec. 12, 2019.
Office Action issued in U.S. Appl. No. 15/639,765, dated Feb. 5, 2021.
Office Action issued in U.S. Appl. No. 15/639,765, dated Jul. 22, 2020.
Office Action issued in U.S. Appl. No. 15/639,765, dated Mar. 5, 2019.

(56) References Cited

OTHER PUBLICATIONS

Pantuck et al., "Optimizing prostate cancer suicide gene therapy using herpes simplex virus thymidine kinase active site variants," *Human Gene Therapy*, 13:777-789, 2002.
PCT International Search Report and Written Opinion issued in corresponding PCT Application No. PCT/US17/40303, dated Oct. 27, 2017.
Qin et al., "Systematic comparison of constitutive promoters and the doxycycline-inducible promoter," *PLoS ONE*, 5(5):e10611, 2010.
Tieng et al., "Elimination of proliferating cells from CNS grafts using a Ki67 promoter-driven thymidine kinase," *Molecular Therapy—Methods & Clinical Development*, 6:1-12, 2016.

\* cited by examiner

SEQUENCE LISTING

<160> NUMBER OF SEQ ID NOS: 30

<210> SEQ ID NO 1
<211> LENGTH: 21
<212> TYPE: DNA
<213> ORGANISM: Artificial sequence
<220> FEATURE:
<223> OTHER INFORMATION: Synthetic primer

<400> SEQUENCE: 1
gagcggtggt tcgacaagtg g          21

<210> SEQ ID NO 2
<211> LENGTH: 19
<212> TYPE: DNA
<213> ORGANISM: Artificial sequence
<220> FEATURE:
<223> OTHER INFORMATION: Synthetic primer

<400> SEQUENCE: 2
cctcagcagg gttggcatc          19

<210> SEQ ID NO 3
<211> LENGTH: 19
<212> TYPE: DNA
<213> ORGANISM: Artificial sequence
<220> FEATURE:
<223> OTHER INFORMATION: Synthetic primer

<400> SEQUENCE: 3
gatgccaacc ctgctgagg          19

<210> SEQ ID NO 4
<211> LENGTH: 19
<212> TYPE: DNA
<213> ORGANISM: Artificial sequence
<220> FEATURE:
<223> OTHER INFORMATION: Synthetic primer

<400> SEQUENCE: 4
gtccagcctg tgctgggtg          19

<210> SEQ ID NO 5
<211> LENGTH: 19

```
<212> TYPE: DNA
<213> ORGANISM: Artificial sequence
<220> FEATURE:
<223> OTHER INFORMATION: Synthetic primer

<400> SEQUENCE: 5
cacccagcac aggctggac                                                19

<210> SEQ ID NO 6
<211> LENGTH: 21
<212> TYPE: DNA
<213> ORGANISM: Artificial sequence
<220> FEATURE:
<223> OTHER INFORMATION: Synthetic primer

<400> SEQUENCE: 6
cagggccaca aaagccagca c                                             21

<210> SEQ ID NO 7
<211> LENGTH: 21
<212> TYPE: DNA
<213> ORGANISM: Artificial sequence
<220> FEATURE:
<223> OTHER INFORMATION: Synthetic primer

<400> SEQUENCE: 7
gtgctggctt ttgtggccct g                                             21

<210> SEQ ID NO 8
<211> LENGTH: 20
<212> TYPE: DNA
<213> ORGANISM: Artificial sequence
<220> FEATURE:
<223> OTHER INFORMATION: Synthetic primer

<400> SEQUENCE: 8
ccagagagct gtccccagtc                                               20

<210> SEQ ID NO 9
<211> LENGTH: 20
<212> TYPE: DNA
<213> ORGANISM: Artificial sequence
<220> FEATURE:
<223> OTHER INFORMATION: Synthetic primer

<400> SEQUENCE: 9
gtcccctgct ggatgcagag                                               20

<210> SEQ ID NO 10
<211> LENGTH: 20
<212> TYPE: DNA
<213> ORGANISM: Artificial sequence
<220> FEATURE:
<223> OTHER INFORMATION: Synthetic primer

<400> SEQUENCE: 10
gtcccctgct ggatgcagag                                               20

<210> SEQ ID NO 11
<211> LENGTH: 153
<212> TYPE: DNA
<213> ORGANISM: Artificial sequence
<220> FEATURE:
<223> OTHER INFORMATION: Synthetic oligonucleotide

<400> SEQUENCE: 11
```

```
atggcttctt accctggaca ccagcatgct tctgcctttg accaggctgc cagatccagg    60
ggccactcca acaggagaac tgccctaaga cccagaagac agcaggaagc cactgaggtg   120
aggcctgagc agaagatgcc aaccctgctg agg                                153
```

<210> SEQ ID NO 12
<211> LENGTH: 153
<212> TYPE: DNA
<213> ORGANISM: Artificial sequence
<220> FEATURE:
<223> OTHER INFORMATION: Synthetic oligonucleotide

<400> SEQUENCE: 12

```
atggcttctt accctggaca ccagcatgct tctgcctttg accaggctgc cagatccagg    60
ggccactcca acaggagaac tgccctaaga cccagaagac agcaggaagc cactgaggtg   120
aggcctgagc agaagatgcc aaccctgctg agg                                153
```

<210> SEQ ID NO 13
<211> LENGTH: 172
<212> TYPE: DNA
<213> ORGANISM: Artificial sequence
<220> FEATURE:
<223> OTHER INFORMATION: Synthetic oligonucleotide

<400> SEQUENCE: 13

```
gtgtacattg atggacctca tggcatgggc aagaccacca ccactcaact gctggtggca    60
ctgggctcca gggatgacat tgtgtatgtg cctgagccaa tgacctactg gagagtgcta   120
ggagcctctg agaccattgc caacatctac accacccagc acaggctgga cc           172
```

<210> SEQ ID NO 14
<211> LENGTH: 171
<212> TYPE: DNA
<213> ORGANISM: Artificial sequence
<220> FEATURE:
<223> OTHER INFORMATION: Synthetic oligonucleotide

<400> SEQUENCE: 14

```
gtgtacattg atggacctca tggcatgggc aagaccacca ccactcaact gctggtggca    60
ctgggctcca gggatgacat tgtgtatgtg cctgagccaa tgacctactg gagagtgcta   120
ggacctctga ccattgcc aacatctaca ccacccagca caggctggac c              171
```

<210> SEQ ID NO 15
<211> LENGTH: 233
<212> TYPE: DNA
<213> ORGANISM: Artificial sequence
<220> FEATURE:
<223> OTHER INFORMATION: Synthetic oligonucleotide

<400> SEQUENCE: 15

```
agggagaaat ctctgctgga gatgctgctg tggtgatgac ctctgcccag atcacaatgg    60
gaatgcccta tgctgtgact gatgctgttc tggctcctca cattggagga gaggctggct   120
cttctcatgc ccctccacct gccctgaccc tgatctttga cagacacccc attgcagccc   180
tgctgtgcta cccagcagca aggtacctca tgggctccat gaccccacag gct          233
```

<210> SEQ ID NO 16
<211> LENGTH: 233
<212> TYPE: DNA
<213> ORGANISM: Artificial sequence
<220> FEATURE:
<223> OTHER INFORMATION: Synthetic oligonucleotide

<400> SEQUENCE: 16

| agggagaaat ctctgctgga gatgctgctg tggtgatgac ctctgcccag atcacaatgg | 60 |
| gaatgcccta tgctgtgact gatgctgttc tggctcctca cattggagga gaggctggct | 120 |
| cttctcatgc ccctccacct gccctgaccc tgatctttga cagacacccc attgcagccc | 180 |
| tgctgtgcta cccagcagca aggtacctca tgggctccat gaccccacag gct | 233 |

<210> SEQ ID NO 17
<211> LENGTH: 232
<212> TYPE: DNA
<213> ORGANISM: Artificial sequence
<220> FEATURE:
<223> OTHER INFORMATION: Synthetic oligonucleotide

<400> SEQUENCE: 17

| gtgctggctt ttgtggccct gatccctcca accctccctg gcaccaacat tgttctggga | 60 |
| gcactgcctg aagacagaca cattgacagg ctggcaaaga ggcagagacc tggagagaga | 120 |
| ctggacctgg ccatgctggc tgcaatcaga agggtgtatg gactgctggc aaacactgtg | 180 |
| agatacctcc agtgtggagg ctcttggaga gaggactggg gacagctctc tg | 232 |

<210> SEQ ID NO 18
<211> LENGTH: 232
<212> TYPE: DNA
<213> ORGANISM: Artificial sequence
<220> FEATURE:
<223> OTHER INFORMATION: Synthetic oligonucleotide

<400> SEQUENCE: 18

| gtgctggctt ttgtggccct gatccctcca accctccctg gcaccaacat tgttctggga | 60 |
| gcactgcctg aagacagaca cattgacagg ctggcaaaga ggcagagacc tggagagaga | 120 |
| ctggacctgg ccatgctggc tgcaatcaga agggtgtatg gactgctggc aaacactgtg | 180 |
| agatacctcc agtgtggagg ctcttggaga gaggactggg gacagctctc tg | 232 |

<210> SEQ ID NO 19
<211> LENGTH: 150
<212> TYPE: DNA
<213> ORGANISM: Artificial sequence
<220> FEATURE:
<223> OTHER INFORMATION: Synthetic oligonucleotide

<400> SEQUENCE: 19

| atgctctgct gcaactaacc tctggcatgg tgcagaccca tgtgaccacc cctggcagca | 60 |
| tccccaccat ctgtgaccta gccagaacct ttgccaggga gatgggaatc tctggagcca | 120 |
| atggagtcat ggccaagttg accagtgctg | 150 |

<210> SEQ ID NO 20
<211> LENGTH: 150
<212> TYPE: DNA
<213> ORGANISM: Artificial sequence
<220> FEATURE:
<223> OTHER INFORMATION: Synthetic oligonucleotide

<400> SEQUENCE: 20

| atgctctgct gcaactaacc tctggcatgg tgcagaccca tgtgaccacc cctggcagca | 60 |
| tccccaccat ctgtgaccta gccagaacct ttgccaggga gatgggaatc tctggagcca | 120 |
| atggagtcat ggccaagttg accagtgctg | 150 |

<210> SEQ ID NO 21
<211> LENGTH: 111
<212> TYPE: DNA
<213> ORGANISM: Artificial sequence
<220> FEATURE:
<223> OTHER INFORMATION: Synthetic oligonucleotide

<400> SEQUENCE: 21
ggctggcaca ggtagaaatc tctgctggag atgctgctgt ggtgatgacc tctgcccaga      60
tcacaatggg aatgccctat gctgtgactg atgctgttct ggctcctcac a              111

<210> SEQ ID NO 22
<211> LENGTH: 111
<212> TYPE: DNA
<213> ORGANISM: Artificial sequence
<220> FEATURE:
<223> OTHER INFORMATION: Synthetic oligonucleotide

<400> SEQUENCE: 22
ggctggcaca gggagaaatc tctgctggag atgctgctgt ggtgatgacc tctgcccaga      60
tcacaatggg aatgccctat gctgtgactg atgctgttct ggctcctcac a              111

<210> SEQ ID NO 23
<211> LENGTH: 111
<212> TYPE: DNA
<213> ORGANISM: Artificial sequence
<220> FEATURE:
<223> OTHER INFORMATION: Synthetic oligonucleotide

<400> SEQUENCE: 23
ggctggcaca gggagaaatc tctgctggag atgctgctgt ggtgatgacc tctgcccaga      60
tcacaatggg aatgccctat gctgtgactg atgctgttct ggctcctcac a              111

<210> SEQ ID NO 24
<211> LENGTH: 111
<212> TYPE: DNA
<213> ORGANISM: Artificial sequence
<220> FEATURE:
<223> OTHER INFORMATION: Synthetic oligonucleotide

<400> SEQUENCE: 24
ggctggcaca gggagaaatc tctgctggag atgctgctgt ggtgatgacc tctgcccaga      60
tcacaatggg aatgccctat gctgtgactg atgctgttct ggctcctcac a              111

<210> SEQ ID NO 25
<211> LENGTH: 111
<212> TYPE: DNA
<213> ORGANISM: Artificial sequence
<220> FEATURE:
<223> OTHER INFORMATION: Synthetic oligonucleotide

<400> SEQUENCE: 25
ggctggcaca gggagaaatc tctgctggag atgctgctgt ggtgatgacc tctgcccaga      60
tcacaatgag aatgccctat gctgtgactg atgctgttct ggctcctcac a              111

<210> SEQ ID NO 26
<211> LENGTH: 111
<212> TYPE: DNA
<213> ORGANISM: Artificial sequence
<220> FEATURE:
<223> OTHER INFORMATION: Synthetic oligonucleotide

<400> SEQUENCE: 26

```
ggctggcaca gggagaaatc tctgctggag atgctgctgt ggtgatgacc tctgcccaga      60
tcacaatggg aatgccctat gctgtgactg atgctgttct ggttcctcac a             111

<210> SEQ ID NO 27
<211> LENGTH: 13
<212> TYPE: PRT
<213> ORGANISM: Artificial sequence
<220> FEATURE:
<223> OTHER INFORMATION: Synthetic peptide

<400> SEQUENCE: 27

Arg Val Tyr Ile Asp Gly Pro His Gly Met Gly Lys Thr
1               5                   10

<210> SEQ ID NO 28
<211> LENGTH: 13
<212> TYPE: PRT
<213> ORGANISM: Artificial sequence
<220> FEATURE:
<223> OTHER INFORMATION: Synthetic peptide

<400> SEQUENCE: 28

Arg Val Tyr Ile Asp Gly Pro His Gly Met Gly Lys Thr
1               5                   10

<210> SEQ ID NO 29
<211> LENGTH: 170
<212> TYPE: DNA
<213> ORGANISM: Artificial sequence
<220> FEATURE:
<223> OTHER INFORMATION: Synthetic oligonucleotide

<400> SEQUENCE: 29 gtccctgct ggatgcagag atgctctgct gcaactaacc tctggcatgg tgcagaccca      60
tgtgaccacc cctggcagca tccccaccat ctgtgaccta gccagaacct tgccaggga    120 gatgggaatc tctggagcca atggagtcat ggccaagttg accagtgctg              170

<210> SEQ ID NO 30
<211> LENGTH: 170
<212> TYPE: DNA
<213> ORGANISM: Artificial sequence
<220> FEATURE:
<223> OTHER INFORMATION: Synthetic oligonucleotide

<400> SEQUENCE: 30 gtccctgct ggatgcagag atgctctgct gcaactaacc tctggcatgg tgcagaccca      60
tgtgaccacc cctggcagca tccccaccat ctgtgaccta gccagaacct tgccaggga    120 gatgggaatc tctggagcca atggagtcat ggccaagttg accagtgctg              170
```

ELIMINATION OF PROLIFERATING CELLS FROM STEM CELL-DERIVED GRAFTS

This application claims the benefit of U.S. Provisional Patent Application No. 62/592,219, filed Nov. 29, 2017, which is incorporated herein by reference in its entirety.

INCORPORATION OF SEQUENCE LISTING

The sequence listing that is contained in the file named "CLFRP0473US_ST25.TXT", which is 8.62 KB (as measured in Microsoft Windows®) and was created on Nov. 29, 2018, is filed herewith by electronic submission and is incorporated by reference herein.

BACKGROUND

1. Field

The present invention relates generally to the field of stem cell therapy. More particularly, it concerns the specific elimination of proliferating cells in stem cell-derived grafts.

2. Description of Related Art

Parkinson's disease (PD) is a neurodegenerative disorder characterized by the loss of the nigrostriatal pathway. Although the cause of Parkinson's disease is not known, it is associated with the progressive degeneration or death of dopaminergic (i.e., tyrosine hydroxylase (TH) positive) neurons in the substantia nigra region of the basal ganglia, which induces progressive deterioration of motor function control. The characteristic symptoms of Parkinson's disease appear when up to 70% of TH-positive nigrostriatal neurons have degenerated.

There is currently no satisfactory cure for Parkinson's disease. Symptomatic treatment of the disease-associated motor impairments involves oral administration of dihydroxyphenylalanine (L-DOPA). L-DOPA is transported across the blood-brain barrier and converted to dopamine, partly by residual dopaminergic neurons, leading to a substantial improvement of motor function. However, after a few years, the degeneration of dopaminergic neurons progresses, the effects of L-DOPA are reduced and symptoms reappear.

Deep brain stimulation (DBS) therapy is the current preferred treatment for Parkinson's disease. DBS is a treatment of Parkinson's disease that aims to change the rates and patterns of activity of brain cells by implanting a brain stimulator (i.e., an electrode) into a target region in the brain known to be associated with movement, such as the subthalamic nucleus, basal ganglia structures, including the globus pallidus internalis, or ventrointermediate nucleus of the thalamus. However, the success of DBS procedures can diminish over time. Therefore, better therapy for Parkinson's disease is necessary.

A treatment method for Parkinson's disease currently in development involves the transplantation of partially differentiated neuroepithelial cells (i.e., neural progenitor cells) into brain regions lacking sufficient dopaminergic signaling; these cells then differentiate into dopaminergic neurons in vivo. The potential of neural progenitor cells to differentiate into dopaminergic neurons was demonstrated both with rodent and human PSC (Kriks et al., 2011; Wernig et al., 2008). Moreover, the potential of PSC-derived neural progenitor cells to reinnervate the striatum in drug-lesioned rodent and primate models of Parkinson's disease was shown (Ganat et al., 2012; Kriks et al., 2011; Wernig et al., 2008).

However, not all transplanted neural progenitor cells differentiate into the desired neuronal subtypes and instead remain as proliferating cells within the graft, which leads to overgrowth and tumor formation. Even the most advanced protocols available (Ganat et al., 2012) have been unable to overcome the problem of residual proliferating cells forming neuroepithelial tumors during PSC-derived neural progenitor cell-based therapy of CNS diseases. Therefore, there is an unmet need for methods of eliminating residual proliferating cells following stem cell-based therapy.

SUMMARY

In certain embodiments, the present disclosure concerns isolated and recombinant polynucleotides, such as polynucleotides comprising a cell-cycle dependent promoter operatively linked to a suicide gene. In one embodiment, there is provided an expression vector comprising a cell cycle-dependent promoter operatively linked to a suicide gene coding sequence, wherein the suicide gene is cytomegalovirus (CMV) UL97 or mutant HSV thymidine kinase (TK). In some aspects, the CMV-UL97 gene is a mutated version of wild-type CMV-UL97 comprising one or more amino acid substitutions. The HSV-TK mutant can have one or more amino acid substitutions at residues 159-161 and 168-169 of HSV TK. The TK mutant used in the present methods may be SR11, SR26, SR39, SR4, SR15, SR32, or SR53 TK mutants. For example, the HSV TK can be HSV1-SR39TK (i.e, $_{159}IFL_{161}$ and $_{168}FM_{169}$, amino acid substitution at position 159 is leucine to isoleucine, at position 160 is isoleucine to phenylalanine, at position 161 is phenylalanine to leucine, at position 168 is alanine to phenylalanine, and at position 169 is leucine to methionine).

In some aspects, the cell cycle-dependent promoter is a Ki-67, PCNA (proliferating cell nuclear antigen), CCNA2 (Cyclin A2), CCNB2 (Cyclin B2), DLGAP5 (DLG associated protein 5), or TOP2A (DNA topoisomerase II alpha) promoter. In some aspects, the cell cycle-dependent promoter is a hybrid of Ki-67, PCNA, CCNA2, CCNB2, DLGAP5, or TOP2A promoters. In particular aspects, the cell cycle-dependent promoter is a Ki-67 promoter.

In some aspects, the expression vector further comprises a selectable marker. In certain aspects, the selectable marker is an antibiotic resistance gene or a gene encoding a fluorescent protein.

In certain aspects, the expression vector is further defined as a viral vector. In some aspects, the viral vector is a lentiviral vector, an adenoviral vector, a retroviral vector, a vaccinia viral vector, an adeno-associated viral vector, a herpes viral vector, or a polyoma viral vector. In particular aspects, the viral vector is a lentiviral vector.

In another embodiment, there is provided a host cell comprising the polynucleotide comprising a cell-cycle dependent promoter operatively linked to a suicide gene. In particular aspects, the host cell is further defined as a precursor cell. In some aspects, the polynucleotide is introduced into the host cell using a viral vector, such as a lentiviral vector, retroviral vector, an adenoviral vector (e.g., an integrating adenovector), a vaccinia viral vector, an adeno-associated viral vector, a herpes viral vector, or a polyoma viral vector. In particular aspects, the viral vector is a lentiviral vector. The vector may be an integrating vector. In other aspects, the polynucleotide is introduced into the host cell using a non-viral approach, such as injection of naked DNA, nucleic acid delivery enhanced by physical methods (e.g., electroporation or gene gun), or nucleic acid delivery enhanced by chemical methods (e.g., lipids, liposomes nanoparticles, or cell permeating peptides).

In some aspects, the host cell is further defined as a neural precursor cell, cardiomyocyte precursor cell, endothelial precursor cell, pancreatic precursor cell, kidney precursor cell, oligodendrocyte precursor cell, hematopoietic precursor cell, myeloid precursor cell, mesenchymal precursor cell, retinal precursor cell, or osteoclast precursor cell. In particular aspects, the host cell is further defined as a neural precursor cell. In some aspects, the cell is derived from a pluripotent stem cell (PSC). In some aspects, the PSC is an induced pluripotent stem cell (iPS cell) or embryonic stem cell (ESC). In particular aspects, the neural precursor cell is further defined as a cell expressing at least one of the markers selected from the group consisting of musashi, nestin, sox2, vimentin, pax6, and sox1. In certain aspects, the neural precursor cell expresses 2, 3, 4, 5, or all 6 of the markers musashi, nestin, sox2, vimentin, pax6, and sox1.

In a further embodiment, there is provided a host cell comprising an expression vector of the embodiments. In some aspects, the host cell is further defined as a neural precursor cell, cardiomyocyte precursor cell, endothelial precursor cell, pancreatic precursor cell, kidney precursor cell, oligodendrocyte precursor cell, hematopoietic precursor cell, myeloid precursor cell, mesenchymal precursor cell, retinal precursor cell, or osteoclast precursor cell. In particular aspects, the host cell is further defined as a neural precursor cell. In some aspects, the cell is derived from a pluripotent stem cell (PSC). In some aspects, the PSC is an induced pluripotent stem cell (iPS cell) or embryonic stem cell (ESC). In particular aspects, the neural precursor cell is further defined as a cell expressing at least one of the markers selected from the group consisting of musashi, nestin, sox2, vimentin, pax6, and sox1. In certain aspects, the neural precursor cell expresses 2, 3, 4, 5, or all 6 of the markers musashi, nestin, sox2, vimentin, pax6, and sox1.

In an even further embodiment, there is provided a pharmaceutical composition comprising the host cell of the embodiments and, optionally, a pharmaceutically acceptable carrier.

In another embodiment, there is provided a method of producing host cells (e.g., precursor cells) of the embodiments comprising obtaining a starting population of PSCs; differentiating the PSCs into precursor cells; and isolating and culturing the precursor cells, wherein either the PSCs or the precursor cells are transfected or transduced with a polynucleotide comprising a cell-cycle dependent promoter operatively linked to a suicide gene (e.g, in an expression vector of the embodiments) and selected for the presence of said polynucleotide (e.g., the expression vector), such that the cultured precursor cells comprise the cell cycle-dependent promoter operatively linked to the suicide gene coding sequence.

In some aspects, the precursor cells are neural precursor cells, cardiomyocyte precursor cells, endothelial precursor cells, pancreatic precursor cells, kidney precursor cells, oligodendrocyte precursor cells, hematopoietic precursor cells, myeloid precursor cells, mesenchymal precursor cells, retinal precursor cells, or osteoclast precursor cells. In certain aspects, the precursor cells are neural precursor cells.

In certain aspects, the pluripotent stem cell population is an embryonic stem cell. In particular aspects, the pluripotent stem cell population is an induced pluripotent stem cell population.

In some aspects, differentiating cells of the population into neural precursor cells comprises contacting the pluripotent stem cell population with fibroblast growth factor or epidermal growth factor.

In certain aspects, the method further comprises contacting the pluripotent stem cell population with N2 and B27. In some aspects, isolating comprises sorting the cells of the population to isolate precursor cells, such as neural progenitor cells.

In some aspects, cells are selected for the presence of said expression vector by a method comprising contacting the transfected or transduced cells with an antibiotic. In certain aspects, cells are selected for the presence of said expression vector by a method comprising sorting the transfected or transduced cells.

A further embodiment provides a method of cell replacement therapy for replacing cells that are known to be essentially non-dividing cells, the method comprising administering an effective amount of host cells (e.g., precursor cells) of the embodiments, and administering to the subject an amount of a prodrug that is activated by the suicide gene, the prodrug being administered in an amount effective to eliminate cycling precursor cells In some aspects, the subject is a mammal. In certain aspects, the mammal is a mouse, rat, non-human primate, or human. In some aspects, the genome of the host cell comprises a genome essentially identical to the genome of the subject and an expression vector of the embodiments. In some aspects, the essentially non-dividing cells to be replaced comprise dopaminergic cells and the precursor cell population comprises dopaminergic neural precursor cells (e.g., defined as expressing tyrosine hydroxylase or dopamine active transporter). In certain aspects, the subject has Parkinson's disease. In particular aspects, the prodrug is ganciclovir and/or acyclovir. In specific aspects, the prodrug is penciclovir In some aspects, the prodrug is administered more than once. In some aspects, the prodrug is administered after a sufficient period of time for the precursor cells to initiate differentiation. In some aspects, the period of time is 3-6 days, such as 3, 4, 5, or 6 days after administering the precursor cells. In other aspects, the period of time is 7-15 days, such as 7, 8, 9, 10, 11, 12, 13, 14, or 15 days after administering the precursor cells. In other aspects, the precursor cells and pro-drug are administered concurrently. In some aspects, the prodrug is administered by injection Other objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figures 1A, 1B, 1C:
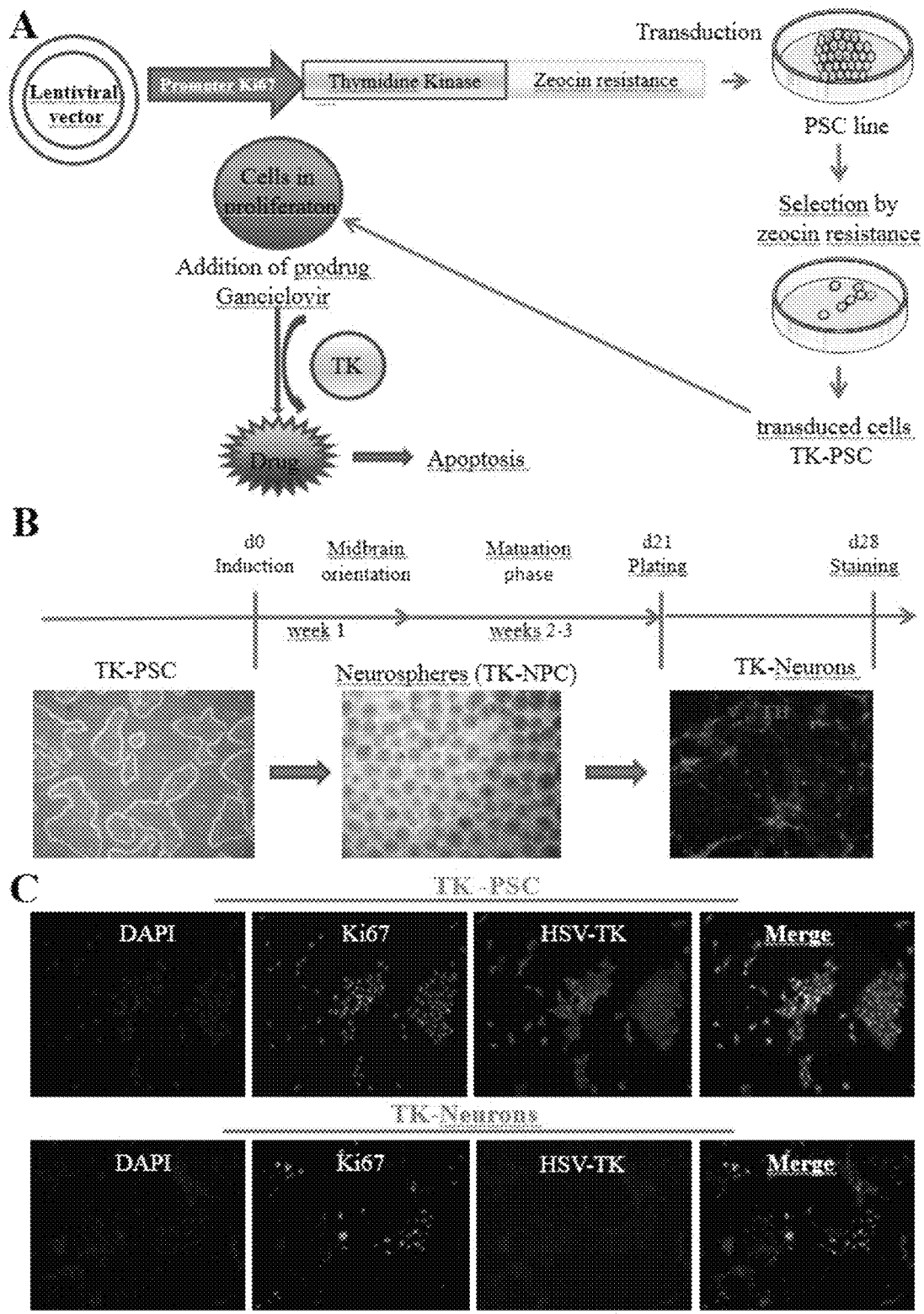
FIGS. 1A-1C: Elaboration of a pluripotent stem cell line expressing a suicide gene under the control of a cell cycle-dependent promoter. (A) Thymidine kinase from herpes simplex virus (HSV-TK) was introduced into a lentiviral vector under the control of a Ki67 promotor fragment. The TK used in this study was a fusion protein containing a C-terminally fused zeocin resistance gene. The construct was transduced into the clinical grade human pluripotent stem cell line HS415 (TK-PSC). TK-PSC cells expressing this enzyme were selected by their resistance to zeocin. (B) Cell preparations used in the present study: pluripotent stem cells (TK-PSC, left panel) were differentiated into neurospheres containing dopaminergic neuroprogenitors (TK-NPC, middle panel) and terminated maturation into dopaminergic neurons (TH staining of TK-neurons, right panel). (C) Characterization of TK-PSC cells in undifferentiated state (upper panel) and upon differentiation into neurons (lower panel). Ki67 and HSV-TK were detected by immunostaining and nucleus by DAPI. Both TK-PSC and TK-Neuron showed staining for Ki67 and HSV-TK which overlap in the merged images.

Pluripotent stem cell (PSC)-based cell therapy is an attractive concept, in particular for neurodegenerative diseases. However, transplantation of undifferentiated PSC or rapidly proliferating precursor cells can lead to tumor formation. Thus, to translate promising animal data into a future clinical use, safety mechanisms to eliminate proliferating cells are needed. Thus, in certain embodiments, the present disclosure provides methods and compositions for a suicide gene approach to eliminate proliferating cells. In an exemplary method, an expression vector is provided based on a cell cycle-dependent promoter (e.g., Ki67) driving the expression of a suicide gene (e.g., cytomegalovirus (CMV) UL97). The present studies show for the first time the use of the CMV-UL97 gene as a suicide gene. Thus, this construct provides methods to render proliferative cells sensitive to ganciclovir after transplantation but avoids expression of the antigenic viral suicide gene protein in post-mitotic neurons.

The present disclosure shows that host cells comprising the exemplary Ki67-HSV-TK construct or CMV-UL97 killed proliferating PSC and early neural precursor cells (NPC) by exposure to ganciclovir, acyclovir, or penciclovir in vitro. In addition, in vivo transplantation of PSC induced a teratoma which was prevented by early (e.g., 4 days post-transplant) treatment with ganciclovir. Thus, the suicide gene approach of the present disclosure allows killing of proliferating undifferentiated and/or overgrowth of early precursor cells without expression of the suicide gene in mature neurons. This approach has the potential to be useful for other stem cell-based therapies, where the final target is a post-mitotic cell (e.g. cardiomyocytes, or pancreatic beta cells).

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

The term "cell" is herein used in its broadest sense in the art and refers to a living body that is a structural unit of tissue of a multicellular organism, is surrounded by a membrane structure that isolates it from the outside, has the capability of self-replicating, and has genetic information and a mechanism for expressing it. Cells used herein may be naturally-occurring cells or artificially modified cells (e.g., fusion cells, genetically modified cells, etc.).

The term "stem cell" refers herein to a cell that under suitable conditions is capable of differentiating into a diverse range of specialized cell types, while under other suitable conditions is capable of self-renewing and remaining in an essentially undifferentiated pluripotent state. The term "stem cell" also encompasses a pluripotent cell, multipotent cell, precursor cell and progenitor cell. Exemplary human stem cells can be obtained from hematopoietic or mesenchymal stem cells obtained from bone marrow tissue, embryonic stem cells obtained from embryonic tissue, or embryonic germ cells obtained from genital tissue of a fetus. Exemplary pluripotent stem cells can also be produced from somatic cells by reprogramming them to a pluripotent state by the expression of certain transcription factors associated with pluripotency; these cells are called "induced pluripotent stem cells," "iPS cells" or "iPSCs".

An "embryonic stem (ES) cell" is an undifferentiated pluripotent stem cell which is obtained from an embryo in an early stage, such as the inner cell mass at the blastocyst stage, or produced by artificial means (e.g. nuclear transfer) and can give rise to any differentiated cell type in an embryo or an adult, including germ cells (e.g. sperm and eggs).

"Induced pluripotent stem cells (iPSCs)" are cells generated by reprogramming a somatic cell by expressing or inducing expression of a combination of factors (herein referred to as reprogramming factors). iPSCs can be generated using fetal, postnatal, newborn, juvenile, or adult somatic cells. In certain embodiments, factors that can be used to reprogram somatic cells to pluripotent stem cells include, for example, Oct4 (sometimes referred to as Oct 3/4), Sox2, c-Myc, Klf4, Nanog, and Lin28. In some embodiments, somatic cells are reprogrammed by expressing at least two reprogramming factors, at least three reprogramming factors, or four reprogramming factors to reprogram a somatic cell to a pluripotent stem cell.

"Pluripotent stem cell" refers to a stem cell that has the potential to differentiate into all cells found in an organism preferably, cells representing any of the three germ layers: endoderm (e.g., interior stomach lining, gastrointestinal tract, and the lungs), mesoderm (e.g., muscle, bone, blood, and urogenital), or ectoderm (e.g., epidermal tissues and nervous system).

As used herein, the term "somatic cell" refers to any cell other than germ cells, such as an egg or a sperm which does not directly transfer its DNA to the next generation. Typically, somatic cells have limited or no pluripotency. Somatic cells used herein may be naturally-occurring or genetically modified.

As used herein the term "engineered" in reference to cells refers to cells that comprise at least one genetic element exogenous to the cell that is integrated into the cell genome. In some aspects, the exogenous genetic element can be integrated at a random location in the cell genome. In other aspects, the genetic element is integrated at a specific site in the genome. For example, the genetic element may be integrated at a specific position to replace an endogenous nucleic acid sequence, such as to provide a change relative to the endogenous sequence (e.g., a change in single nucleotide position).

A "precursor cell" as used herein refers to a stem cell which has the potential to differentiate into many different (pluri- and multipotent) or two different (bipotent) mature cell types. A precursor cell may also be a stem cell which has the capacity to differentiate into only one cell type. For example, precursor cells include neural precursor cells (NPCs), cardiomyocyte precursor cells and pancreatic precursor cells. "Neural precursor cells" are defined herein as immature cells of the nervous system which have the potential to develop into mature nervous system cells such as neurons and glia (e.g., astrocytes and oligodendrocytes).

The term "suicide gene" refers to a gene whose protein product converts a non-toxic prodrug into a toxic drug (e.g., an active chemotherapeutic agent), thereby killing cells that express the gene product.

As used herein, the term "polynucleotide" refers to a nucleic acid molecule that either is recombinant or has been isolated free of total genomic nucleic acid. By "isolated" when referring to a nucleotide sequence, is meant that the indicated molecule is present in the substantial absence of other biological macromolecules of the same type. Included within the term "polynucleotide" are recombinant vectors, including, for example, plasmids, cosmids, phage, viruses, and the like. Polynucleotides include, in certain aspects, regulatory sequences, isolated substantially away from their naturally occurring genes or protein coding sequences. Polynucleotides may be single-stranded (coding or antisense) or double-stranded, and may be RNA, DNA (e.g., genomic DNA, cDNA, or synthetic DNA), analogs thereof, or a combination thereof. Additional coding or non-coding sequences may, but need not, be present within a polynucleotide.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operatively linked coding sequence in a particular host organism, including, but not limited to, promoter regions, polyadenylation signals, transcription termination sequences, upstream regulatory domains, internal ribosome entry sites (IRES), enhancers, and the like. In addition to control sequences that govern transcription and translation, vectors and expression vectors may contain nucleic acid sequences that serve other functions as well, such as origins of replication for the replication of a vector in a recipient cell. Not all of these control elements need always be present so long as the selected coding sequence is capable of being replicated, transcribed, and translated in an appropriate host cell.

The term "promoter region" is used herein in its ordinary sense to refer to a nucleotide region comprising a DNA regulatory sequence, wherein the regulatory sequence is derived from a gene that is capable of binding RNA polymerase and other transcription factors and initiating transcription of a downstream coding sequence. Promoter regions also control the rate of transcription. A promoter may or may not be used in conjunction with an "enhancer," which refers to a cis-acting regulatory sequence involved in the transcriptional activation of a nucleic acid sequence. "Operatively linked" refers to an arrangement of elements wherein the components so described are configured so as to perform their usual function. Thus, control sequences operatively linked to a coding sequence are capable controlling the transcriptional initiation and expression of that sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operatively linked" to the coding sequence.

The term "heterologous," as it relates to nucleic acid sequences, such as gene sequences and control sequences, denotes sequences that are not normally joined together and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct that is not normally present in the cell would be considered heterologous for purposes of the present disclosure. Allelic variation or naturally occurring mutational events do not give rise to heterologous DNA, as used herein.

For the purpose of describing the relative position of nucleotide sequences in a particular nucleic acid molecule throughout the present application, such as when a particular nucleotide sequence is described as being situated "upstream," "downstream," "5'," or "3'" relative to another sequence, it is to be understood that it is the position of the sequences in the non-transcribed strand of a DNA molecule that is being referred to as is conventional in the art.

"Homology" refers to the percent identity between two polynucleotide moieties. Two polynucleotide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified polynucleotide sequence.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. *Gene* 13: 197, 1981. Such techniques can be used to introduce one or more exogenous DNA moieties, such as a plasmid vector and other nucleic acid molecules, into suitable host cells. The term refers to both stable and transient uptake of the genetic material.

The term "transduction" denotes the delivery of a DNA molecule to a recipient cell either in vivo or in vitro, via a replication-defective viral vector, such as via a recombinant lentiviral vector particle.

By "vertebrate subject" is meant any member of the subphylum chordata, including, without limitation, mammals such as cattle, sheep, pigs, goats, horses, and human and non-human primates; domestic animals such as dogs and cats; laboratory animals including rodents such as mice, rats and guinea pigs, and the like; birds, including domestic, wild and game birds such as cocks and hens including chickens, turkeys and other gallinaceous birds; and fish. The term does not denote a particular age. Thus, both adult and newborn animals, as well as fetuses, are intended to be covered.

By "subject" or "patient" is meant any single subject for which therapy is desired, including humans, cattle, dogs, guinea pigs, rabbits, chickens, and so on. Also intended to be included as a subject are any subjects involved in clinical research trials not showing any clinical sign of disease, or subjects involved in epidemiological studies, or subjects used as controls.

Within the context of the present disclosure, the term "thymidine kinase mutant" should be understood to include not only the specific protein described herein (as well as the nucleic acid sequences which encode these proteins), but derivatives thereof which may include various structural forms of the primary protein which retain biological activity. For example, a thymidine kinase mutant may be in the form of acidic or basic salts, or in neutral form. In addition, individual amino acid residues may be modified by oxidation or reduction. Furthermore, various substitutions, deletions, or additions may be made to the amino acid or nucleic acid sequences, the net effect of which is to retain or further enhance the increased biological activity of the mutant. Due to code degeneracy, for example, there may be considerable variation in nucleotide sequences encoding the same amino acid sequence.

II. CELLS OF THE PRESENT DISCLOSURE

In certain embodiments of the present disclosure, there are disclosed methods and compositions for producing precursor cells, such as neural precursor cells, comprising a construct with a cell-cycle dependent promoter operatively linked to a suicide gene, such as HSV-TK or CMV-UL97. In some aspects, the precursor cells are derived from a starting population of pluripotent stem cells (PSCs), such as embryonic stem cells or induced pluripotent stem cells.

A. Pluripotent Stem Cells

The starting population of PSCs of the present disclosure can be human embryonic stem cells (ESCs) or induced pluripotent stem cells (iPSC). Both ESCs and iPSCs are capable of long-term proliferation in vitro, while retaining the potential to differentiate into all cell types of the body, including neural precursor cells, cardiomyocytes, pancreatic beta cells, and hepatocytes. Certain aspects of the present disclosure concern precursor cells that could be induced directly from human ESC or iPSCs via expression of a combination of transcription factors for differentiation/function, similar to the generation of iPSCs, bypassing most, if not all, normal developmental stages.

1. Embryonic Stem Cells

In certain aspects, the precursor cells are derived from ESCs. ESCs are derived from the inner cell mass of blastocysts and have a high in vitro differentiating capability. ESCs can be isolated by removing the outer trophectoderm layer of a developing embryo, then culturing the inner mass cells on a feeder layer of non-growing cells. The replated cells can continue to proliferate and produce new colonies of ESCs which can be removed, dissociated, replated again and allowed to grow. This process of "subculturing" undifferentiated ES cells can be repeated a number of times to produce cell lines containing undifferentiated ES cells (U.S. Pat. Nos. 5,843,780; 6,200,806; 7,029,913). ESCs have the potential to proliferate while maintaining their pluripotency. For example, ESCs are useful in research on cells and on genes which control cell differentiation. The pluripotency of ESCs combined with genetic manipulation and selection can be used for gene analysis studies in vivo via the generation of transgenic, chimeric, and knockout mice.

Methods for producing mouse ESCs are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ESCs. In some methods, mouse ESCs can be grown in the absence of a feeder layer by adding the cytokine leukemia inhibitory factor (LIF) to serum-containing culture medium (Smith, 2000). In other methods, mouse ESCs can be grown in serum-free medium in the presence of bone morphogenetic protein and LIF (Ying et al., 2003).

Human ESCs can be produced or derived from a zygote or blastocyst-staged mammalian embryo produced by the fusion of a sperm and egg cell, nuclear transfer, pathogenesis, or the reprogramming of chromatin and subsequent incorporation of the reprogrammed chromatin into a plasma membrane to produce an embryonic cell by previously described methods (Thomson and Marshall, 1998; Reubinoff et al., 2000). In one method, human blastocysts are exposed to anti-human serum, and trophectoderm cells are lysed and removed from the inner cell mass which is cultured on a feeder layer of mouse embryonic fibroblasts. Further, clumps of cells derived from the inner cell mass are chemically or mechanically dissociated, replated, and colonies with undifferentiated morphology are selected by micropipette, dissociated, and replated. In some methods, human ESCs can be grown without serum by culturing the ESCs on a feeder layer of fibroblasts in the presence of basic fibroblast growth factor (Amit et al., 2000). In other methods, human ESCs can be grown without a feeder cell layer by culturing the cells on a protein matrix such as MATRI-GEL™ or laminin in the presence of "conditioned" medium containing basic fibroblast growth factor (Xu et al., 2001).

ESCs can also be derived from other organisms including rhesus monkey and marmoset by previously described methods (Thomson, and Marshall, 1998; Thomson et al., 1995; Thomson and Odorico, 2000; U.S. Pat. No. 5,843,780), as well as from established mouse and human cell lines. For example, established human ESC lines include MAOI, MA09, ACT-4, HI, H7, H9, H13, H14 and ACT30. As a further example, mouse ESC lines that have been established include the CGR8 cell line established from the inner cell mass of the mouse strain 129 embryos, and cultures of CGR8 cells can be grown in the presence of LIF without feeder layers.

ESCs can be detected by protein markers including transcription factor Oct4, alkaline phosphatase (AP), stage-specific embryonic antigen SSEA-1, stage-specific embryonic antigen SSEA-3, stage-specific embryonic antigen SSEA-4, transcription factor NANOG, tumor rejection antigen 1-60 (TRA-1-60), tumor rejection antigen 1-81 (TRA-1-81), SOX2, or REX1.

2. Induced Pluripotent Stem Cells

In other aspects, the precursor cells are derived from induced pluripotent stem cells, commonly abbreviated iPS cells or iPSCs. The induction of pluripotency was originally achieved in 2006 using mouse cells (Yamanaka et al. 2006) and in 2007 using human cells (Yu et al. 2007; Takahashi et al. 2007) by reprogramming of somatic cells via the introduction of transcription factors that are linked to pluripotency. The use of iPSCs circumvents most of the ethical and practical problems associated with large-scale clinical use of ES cells, and patients with iPSC-derived autologous transplants may not require lifelong immunosuppressive treatments to prevent graft rejection.

With the exception of certain cell types (such as germ cells and enucleated erythrocytes), any cell can be used as a starting point for iPSCs. For example, cell types could be neurons, keratinocytes, fibroblasts, hematopoietic cells, mesenchymal cells, liver cells, or stomach cells. There is no limitation on the degree of cell differentiation or the age of an animal from which cells are collected; even undifferentiated progenitor cells (including somatic stem cells) and finally differentiated mature cells can be used as sources of somatic cells in the methods disclosed herein. The somatic cell can be an adult or a fetal somatic cell. iPSCs can be grown under conditions that are known to differentiate human ESCs into specific cell types, and express human ESC markers including: SSEA-1, SSEA-3, SSEA-4, TRA-1-60, and TRA-1-81.

Somatic cells can be reprogrammed to produce induced pluripotent stem cells (iPSCs) using methods known to one of skill in the art. One of skill in the art can readily produce induced pluripotent stem cells, see for example, U.S. Patent Publication Nos. 20090246875, 201000210014; 20120276636; U.S. Pat. Nos. 8,058,065, 8,129,187, 8,278,620, 8,268,630; and PCT Publication No. WO 2007069666, which are incorporated herein by reference. Generally, nuclear reprogramming factors are used to produce pluripotent stem cells from a somatic cell. Reprogramming factors known in the art include Klf4, c-Myc, Oct3/4, Sox2, Nanog, and Lin28. Any combination of factors may be used in the present methods.

Mouse and human cDNA sequences of these nuclear reprogramming substances are available with reference to the NCBI accession numbers mentioned in U.S. Pat. No. 8,183,038 and PCT Publication No. WO 2007069666, which are incorporated herein by reference. Methods for introducing one or more reprogramming substances, or nucleic acids encoding these reprogramming substances, are known in the art, and disclosed for example, in published U.S. Pat. Nos. 8,071,369, 8,268,620, 8,691,574, 8,741,648, 8,546,140, 8,900,871 and 9,175,268, which are incorporated herein by reference.

Once derived, iPSCs can be cultured in a medium sufficient to maintain pluripotency. The iPSCs may be used with various media and techniques developed to culture pluripotent stem cells, more specifically, embryonic stem cells, as described in U.S. Pat. No. 7,442,548 and U.S. Patent Publication. No. 20030211603. In the case of mouse cells, the culture may be carried out with the addition of Leukemia Inhibitory Factor (LIF) as a differentiation suppression factor to an ordinary medium. In the case of human cells, basic fibroblast growth factor (bFGF) may be added in place of LIF. Other methods for the culture and maintenance of iPSCs, as would be known to one of skill in the art, may be used with the present disclosure.

In certain embodiments, undefined conditions may be used; for example, pluripotent cells may be cultured on fibroblast feeder cells or a medium that has been exposed to fibroblast feeder cells in order to maintain the stem cells in an undifferentiated state. In some embodiments, the cell is cultured in the co-presence of mouse embryonic fibroblasts treated with radiation or an antibiotic to terminate the cell division, as feeder cells. Alternately, pluripotent cells may be cultured and maintained in an essentially undifferentiated state using a defined, feeder-independent culture system, such as a TESR™ medium (Ludwig et al., 2006a; Ludwig et al., 2006b) or E8™/Essential 8™ medium (Chen et al., 2011).

Plasmids have been designed with a number of goals in mind, such as achieving regulated high copy number and avoiding potential causes of plasmid instability in bacteria, and providing means for plasmid selection that are compatible with use in mammalian cells, including human cells. Particular attention has been paid to the dual requirements of plasmids for use in human cells. First, they are suitable for maintenance and fermentation in *E. coli*, so that large amounts of DNA can be produced and purified. Second, they are safe and suitable for use in human patients and animals. The first requirement calls for high copy number plasmids that can be selected for and stably maintained relatively easily during bacterial fermentation. The second requirement calls for attention to elements such as selectable markers and other coding sequences. In some embodiments, plasmids that encode a marker are composed of: (1) a high copy number replication origin, (2) a selectable marker, such as, but not limited to, the neo gene for antibiotic selection with kanamycin, (3) transcription termination sequences, including the tyrosinase enhancer and (4) a multicloning site for incorporation of various nucleic acid cassettes; and (5) a nucleic acid sequence encoding a marker operably linked to the tyrosinase promoter. There are numerous plasmid vectors that are known in the art for inducing a nucleic acid encoding a protein. These include, but are not limited to, the vectors disclosed in U.S. Pat. Nos. 6,103,470; 7,598,364; 7,989,425; and 6,416,998, which are incorporated herein by reference.

An episomal gene delivery system can be a plasmid, an Epstein-Barr virus (EBV)-based episomal vector (U.S. Pat. No. 8,546,140), a yeast-based vector, an adenovirus-based vector, a simian virus 40 (SV40)-based episomal vector, a bovine papilloma virus (BPV)-based vector, or a lentiviral vector. A viral gene delivery system can be an RNA-based or DNA-based viral vector (PCT/JP2009/062911, PCT/JP2011/069588; incorporated herein by reference).

3. Embryonic Stem Cells Derived by Somatic Cell Nuclear Transfer

Pluripotent stem cells for deriving the starting population of host cells could also be prepared by means of somatic cell nuclear transfer, in which a donor nucleus is transferred into a spindle-free oocyte. Stem cells produced by nuclear transfer are genetically identical to the donor nuclei. In one method, donor fibroblast nuclei from skin fibroblasts of a rhesus macaque are introduced into the cytoplasm of spindle-free, mature metaphase II rhesus macaque ooctyes by electrofusion (Byrne et al., 2007). The fused oocytes are activated by exposure to ionomycin, then incubated until the blastocyst stage. The inner cell mass of selected blastocysts are then cultured to produce embryonic stem cell lines. The embryonic stem cell lines show normal ES cell morphology, express various ES cell markers, and differentiate into multiple cell types both in vitro and in vivo.

B. Precursor Cells

Certain embodiments of the present disclosure concern precursor cells comprising a vector encoding a suicide gene under the control of a cell-cycle dependent promoter. The precursor cells may be differentiated from PSCs. Exemplary precursor cells include neural precursor cells (NPCs), cardiomyocyte precursor cells and pancreatic precursor cells.

Neural precursor cells may be differentiated from PSCs using methods known in the art such as, but not limited to, the method disclosed in U.S. Pat. No. 7,968,337; incorporated herein by reference. In brief, the PSCs are cultured in a first medium comprising basic fibroblast growth factor (bFGF), a second medium comprising bFGF and epidermal growth factor (EGF), and a third medium comprising bFGF and platelet-derived growth factor (PDGF) to obtain neural precursor cells. The NPCs can be detected and/or isolated using markers such as musashi, nestin, sox2, vimentin, pax6, and sox1. The NPCs can also be further differentiated to express a variety of neuronal markers, e.g., MAP2, beta-III-tubulin, synapsin, cholinacetyltransferase, tyrosin hydroxylase, GABA, glutamate, serotonin, peripherin and calbindin. Maturation and survival of the differentiated neurons can be enhanced by addition of neurotrophins, e.g., BDNF or neurotrophin 3 (NT-3). Additional methods for the production and culturing of NPCs can be found, for example, in U.S. Pat. Nos. 8,093,053; 5,980,885; 7,968,337 and 8,178,349 and U.S. Application No. 20100323444; each of which is incorporated herein by reference.

III. POLYNUCLEOTIDES OF THE PRESENT DISCLOSURE

In certain embodiments, the present disclosure concerns isolated and recombinant polynucleotides, such as polynucleotides comprising a cell cycle-dependent promoter operatively linked to a suicide gene. In particular embodiments, the present disclosure concerns isolated nucleic acids and recombinant vectors incorporating nucleic acid sequences that encode a suicide gene, the expression of which is operatively linked to a cell cycle-dependent promoter. The term "recombinant" may be used in conjunction with a polynucleotide or polypeptide and generally refers to a polypeptide or polynucleotide produced and/or manipulated in vitro or that is a replication product of such a molecule.

A nucleic acid may be made by any technique known to one of ordinary skill in the art. Non-limiting examples of a synthetic nucleic acid, particularly a synthetic oligonucleotide, include a nucleic acid made by in vitro chemical synthesis using phosphotriester, phosphite or phosphoramidite chemistry and solid phase techniques such as described in EP 266,032, or via deoxynucleoside H-phosphonate intermediates as described by Froehler et al., 1986, and U.S. Pat. No. 5,705,629. A non-limiting example of enzymatically produced nucleic acid includes one produced by enzymes in amplification reactions such as PCR™ (see for example, U.S. Pat. Nos. 4,683,202 and 4,682,195), or the synthesis of oligonucleotides described in U.S. Pat. No. 5,645,897. A non-limiting example of a biologically produced nucleic acid includes recombinant nucleic acid production in living cells, such as recombinant DNA vector production in bacteria (see for example, Sambrook et al. 1989).

The nucleic acids used in the present disclosure can be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol.

A. Nucleic Acid Delivery

The polynucleotides of the present disclosure may be introduced (e.g., transfected or transduced) into a host cell by viral or non-viral methods. Vectors provided herein are designed, primarily, to express a suicide gene under the control of a cell-cycle dependent promoter. One of skill in the art would be well-equipped to construct a vector through standard recombinant techniques (see, for example, Sambrook et al., 2001 and Ausubel et al., 1996, both incorporated herein by reference). Vectors include but are not limited to, plasmids, cosmids, viruses (e.g., bacteriophage, animal viruses, and plant viruses), artificial chromosomes (e.g., YACs), retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus vectors, herpes virus vectors, vaccinia virus vectors, Harvey murine sarcoma virus vectors, murine mammary tumor virus vectors, Rous sarcoma virus vectors, parvovirus vectors, polio virus vectors, vesicular stomatitis virus vectors, maraba virus vectors and group B adenovirus enadenotucirev vectors.

1. Viral Vectors

Viral vectors encoding a cell cycle-dependent promoter operatively linked to a suicide gene may be provided in certain aspects of the present disclosure. In generating recombinant viral vectors, non-essential genes are typically replaced with a gene or coding sequence for a heterologous (or non-native) protein. A viral vector is a kind of expression construct that utilizes viral sequences to introduce nucleic acid and possibly proteins into a cell. The ability of certain viruses to infect cells or enter cells via receptor-mediated endocytosis, and to integrate into host cell genomes and express viral genes stably and efficiently have made them attractive candidates for the transfer of foreign nucleic acids into cells (e.g., mammalian cells). Non-limiting examples of virus vectors that may be used to deliver a nucleic acid of certain aspects of the present disclosure are described below. "Recombinant viral vectors" in the present disclosure refers to viral vectors constructed by genetic recombination techniques. Viral vectors constructed using packaging cells and DNAs encoding a viral genome are called recombinant viral vectors.

i. Retroviral Vectors

In one aspect of the present disclosure, retroviral constructs are provided comprising a 5' long terminal repeat (LTR), a tRNA binding site, a packaging signal, one or more heterologous sequences, an origin of second strand DNA synthesis and a 3' LTR, wherein the vector construct lacks gag/pol and/or env coding sequences.

Heterologous sequences that are included in the vector construct are those that encode a protein, preferably a suicide gene, such as herpes simplex virus thymidine kinase. Within certain embodiments of the present disclosure, the expression cassette described herein may be contained within a plasmid construct.

A retroviral vector of the present disclosure includes at least one expression cassette, which is an assembly that is capable of directing the expression of the sequences(s) or gene(s) of interest. The expression cassette includes a transcriptional promoter region or promoter/enhancer that is operatively linked to the sequence(s) or gene(s) of interest, and may include a polyadenylation sequence as well. Such vector constructs also include a packaging signal, LTRs or functional portions thereof, and positive and negative strand primer binding sites appropriate to the retrovirus used. Optionally, the recombinant retroviral vector may also include a selectable and/or non-selectable marker, an origin of second strand DNA synthesis, a signal that allows the plasmid construct to exist as single-stranded DNA (e.g., a M13 origin of replication), a bacterial origin of replication, and a mammalian origin of replication (e.g., a SV40 or adenovirus origin of replication), one or more restriction sites, and a translation termination sequence. Examples of selectable and non-selectable markers include, but are not limited to, neomycin (Neo), thymidine kinase (TK), hygromycin, phleomycin, puromycin, histidinol, green fluorescent protein (GFP), human placental alkaline phosphatase (PLAP), DHFR, β-galactosidase, and human growth hormone (hGH).

In retroviruses, the LTR may also be modified. The LTR is a retrovirus-specific sequence, which is present at both ends of the viral genome. The 5' LTR serves as a promoter, enhancing proviral mRNA transcription. Thus, it may be possible to enhance mRNA transcription of the gene transfer vector, improve packaging efficiency, and increase vector titer if the portion exhibiting the 5' LTR promoter activity in the gene transfer vector is substituted with another promoter having stronger promoter activity. Furthermore, for example, in the case of lentiviruses, the viral protein tat is known to enhance 5' LTR transcription activity, and therefore, substitution of the 5' LTR with a promoter independent of the tat protein will enable the exclusion of tat from the packaging vectors. After RNAs of viruses that have infected or invaded cells are reverse transcribed, the LTRs at both ends are linked to form a closed circular structure, viral integrase couples with the linkage site, and this structure is then integrated into cell chromosomes. The transcribed proviral mRNAs consist of the region ranging from the 5' LTR transcription initiation site to the 3' LTR polyadenylation sequence located downstream. The 5' LTR promoter portion is not packaged in the virus. Thus, even if the promoter is replaced with another sequence, the portion integrated into target cell chromosomes is unchanged. Based on the facts described above, substitution of the 5' LTR promoter is thought to provide a safer vector with a higher titer. Thus, substitution of the promoter at the 5' end of a gene transfer vector can increase the titer of a packageable vector.

Safety can be improved in recombinant retroviral virus vectors by preventing transcription of the full-length vector mRNA in target cells. This is achieved using a self-inactivating vector (SIN vector) prepared by partially eliminating the 3' LTR sequence. The provirus that has invaded the target cell chromosomes has its 5' end bound to the U3 portion of its 3' LTR. Thus, the U3 portion is located at the 5' end in the gene transfer vector, and from that point, the entire RNA of the gene transfer vector is transcribed. If there are retroviruses or similar proteins in target cells, it is possible that the gene transfer vector may be re-packaged and infect other cells. There is also a possibility that the 3' LTR promoter may express host genes located downstream of the viral genome. When the 3' LTR U3 portion is deleted from a gene transfer vector, target cells lack the promoters of 5' LTR and 3' LTR, thereby preventing the transcription of the full-length viral RNA and host genes. Furthermore, since only the genes of interest are transcribed from endogenous promoters, highly safe vectors capable of high expression can be expected. Such vectors are preferable in the present disclosure. SIN vectors can be constructed according to known methods.

SIN vectors have the added advantage of overcoming the gradual decrease in expression of introduced genes resulting from host methylation of LTR sequences after integration (Challita, P. M. and Kohn, D. B., Proc. Natl. Acad. Sci. USA 91: 2567, 1994). LTR methylation hardly reduces gene expression level in SIN vectors. This is because the vector loses most of the LTR sequence upon integration into the host genome. A SIN vector prepared by substituting another promoter sequence for the 3' LTR U3 region of a gene transfer vector was found to maintain a stable expression for more than two months after introduction into primate ES cells (WO 02/101057). Thus, a SIN vector designed to self-inactivate by the modification of the LTR U3 region may be used in the present disclosure.

Retroviruses can be produced by transcribing in host cells gene transfer vector DNAs which contain a packaging signal and forming virus particles in the presence of gag, pol and envelope proteins. The packaging signal sequence encoded by the gene transfer vector DNAs should preferably be sufficient in length to maintain the structure formed by the sequence. However, in order to suppress the frequency of wild-type virus formation, which occurs due to recombination of the vector DNA packaging signal and the packaging vector supplying the gag and pol proteins, it is also necessary to keep sequence overlapping between these vector sequences to a minimum. Therefore, when it comes to the construction of the gene transfer vector DNAs, it is preferable to use a sequence which is as short as possible and yet still contains the sequence essential for packaging, to ensure packaging efficiency and safety.

The SIV vectors may be replication-incompetent viruses from which 40% or more, more preferably 50% or more, still more preferably 60% or more, even more preferably 70% or more, and most preferably 80% or more of the sequence derived from the original SIV genome has been removed.

In a gene transfer vector DNA, the gag protein has been modified such that it is not expressed. Viral gag protein may be detected by a living body as a foreign substance, and thus as a potential antigen. Alternatively, the protein may affect cellular functions. To prevent gag protein expression, nucleotides downstream of the gag start codon can be added or deleted, introducing modifications which will cause a frameshift. It is also preferable to delete portions of the coding region of the gag protein. The 5' portion of the coding region of the gag protein is known to be essential for virus packaging. Thus, in a gene transfer vector, it is preferable that the C-terminal side of the gag protein-coding region has been deleted. It is preferable to delete as large a portion of the gag coding region as possible, so long as the deletion does not considerably affect the packaging efficiency. It is also preferable to replace the start codon (ATG) of the gag protein with a codon other than ATG. The replacement codon can be selected appropriately so as not to greatly affect the packaging efficiency. A viral vector can be produced by introducing the constructed gene transfer vector DNA, which comprises the packaging signal, into appropriate packaging cells. The viral vector produced can be recovered from, for example, the culture supernatant of packaging cells.

"Packaging cell" refers to a cell that contains those elements necessary for production of infectious recombinant retrovirus that are lacking in a recombinant retroviral vector. Packaging cells contain one or more expression cassettes that are capable of expressing proteins that encode gag, pol, and env-derived proteins. Packaging cells can also contain expression cassettes encoding one or more of vif, rev, or ORF 2 in addition to gag/pol and env expression cassettes.

There is no limitation on the type of packaging cell, as long as the cell line is generally used in viral production. When used for human gene therapy, a human- or monkey-derived cell is suitable. Human cell lines that can be used as packaging cells include, for example, 293 cells, 293T cells, 293EBNA cells, SW480 cells, u87MG cells, HOS cells, C8166 cells, MT-4 cells, Molt-4 cells, HeLa cells, HT1080 cells, and TE671 cells. Monkey cell lines include, for example, COS1 cells, COST cells, CV-1 cells, and BMT10 cells.

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Recombinant lentiviral vectors are capable of infecting non-dividing cells and can be used for both in vivo and ex vivo gene transfer and expression of nucleic acid sequences. For example, recombinant lentivirus capable of infecting a non-dividing cell—wherein a suitable host cell is transfected with two or more vectors carrying the packaging functions, namely gag, pol and env, as well as rev and tat—is described in U.S. Pat. No. 5,994,136, incorporated herein by reference.

The pseudotyped lentiviral vectors of the present disclosure can be purified to become substantially pure. The phrase "substantially pure" means that the pseudotyped lentiviral vectors contain substantially no replicable virus other than the lentivirus. The purification can be achieved using known purification and separation methods such as filtration, centrifugation, and column purification. For example, a vector can be precipitated and concentrated by filtering a vector solution with a 0.45-μm filter, and then centrifuging it at 42500×g at 4° C. for 90 minutes. If necessary, the pseudotyped lentiviral vectors of the present disclosure can be prepared as compositions by appropriately combining with desired pharmaceutically acceptable carriers or vehicle. Specifically, the vector can be appropriately combined with, for example, sterilized water, physiological saline, culture medium, serum, and phosphate buffered saline (PBS). The vector can also be combined with a stabilizer, biocide, and such. Compositions containing a pseudotyped lentiviral vector of the present disclosure are useful as reagents or pharmaceuticals. For example; compositions of the present disclosure can be used as reagents for gene transfer into airway stem cells, or as pharmaceuticals for gene therapy of various diseases such as genetic diseases.

Within one aspect of the present disclosure, retroviral gene delivery vehicles are provided that are constructed to carry or express a selected gene(s) or sequence(s) of interest. Briefly, retroviral gene delivery vehicles of the present disclosure may be readily constructed from a wide variety of retroviruses, including, for example, B, C, and D type retroviruses as well as spumaviruses and lentiviruses, such as FIV, HIV-1, HIV-2, EIAV, and SIV (see RNA Tumor Viruses, Second Edition, Cold Spring Harbor Laboratory, 1985). Such retroviruses may be readily obtained from depositories or collections, such as the American Type Culture Collection ("ATCC"; 10801 University Blvd., Manassas, Va. 20110-2209), or isolated from known sources using commonly available techniques. Any of the above retroviruses may be readily utilized in order to assemble or construct retroviral gene delivery vehicles given the disclosure provided herein, and standard recombinant techniques (e.g., Sambrook et al, Molecular Cloning: A Laboratory Manual, 2d ed., Cold Spring Harbor Laboratory Press, 1989; Kunkle, PNAS 52:488, 1985). In addition, within certain embodiments of the present disclosure, portions of the retroviral gene delivery vehicles may be derived from different retroviruses. For example, within one embodiment of the present disclosure, retroviral LTRs may be derived from a murine sarcoma virus, a tRNA binding site from a Rous sarcoma virus, a packaging signal from a murine leukemia virus, and an origin of second strand synthesis from an avian leukosis virus.

Within certain embodiments of the present disclosure, retroviral vectors are provided wherein viral promoters, preferably CMV or SV40 promoters and/or enhancers are utilized to drive expression of one or more genes of interest. Within other aspects of the present disclosure, retroviral vectors are provided wherein tissue-specific promoters are utilized to drive expression of one or more genes of interest.

Retrovirus vector constructs for use with the present disclosure may be generated such that more than one gene of interest is expressed and preferably secreted. This may be accomplished through the use of di- or oligo-cistronic cassettes (e.g., where the coding regions are separated by 120 nucleotides or less, see generally Levin et al., *Gene* 108: 167-174, 1991), or through the use of internal ribosome entry sites ("IRES").

Within one aspect of the present disclosure, self-inactivating (SIN) vectors are made by deleting promoter and enhancer elements in the U3 region of the 3' LTR, including the TATA box, and binding sites for one or more transcription factors. The deletion is transferred to the 5' LTR after reverse transcription and integration in transduced cells. This results in the transcriptional inactivation of the LTR in the provirus. Possible advantages of SIN vectors include increased safety of the gene delivery system as well as the potential to reduce promoter interference between the LTR and the internal promoter, which may result in increased expression of the gene of interest. Furthermore, it is reasonable to expect tighter control of inducible gene therapy vectors due to the lack of an upstream promoter element in the 5' LTR.

Within one aspect of the present disclosure, lentiviral vector constructs are provided comprising a 5' LTR, a tRNA binding site, a packaging signal, one or more heterologous sequences, an origin of second strand DNA synthesis, an RNA export element, and a 3' LTR. Briefly, long terminal repeats ("LTRs") are subdivided into three elements, designated U5, R, and U3. These elements contain a variety of signals that are responsible for the biological activity of a retrovirus, including for example, promoter and enhancer elements that are located within U3. LTRs may be readily identified in the provirus (integrated DNA form) due to their precise duplication at either end of the genome. For purposes of the present disclosure, a 5' LTR should be understood to include as much of the native 5' LTR as is required to function as a 5' promoter or promoter/enhancer element, to allow reverse transcription, and to allow integration of the DNA form of the vector. The 3' LTR should be understood to include as much of the 3' FIV LTR as is required to function as a polyadenylation signal, to allow reverse transcription, and to allow integration of the DNA form of the vector.

Additionally, retroviral vectors may contain hybrid LTRs where up to 75% of the wild-type LTR sequence is deleted and replaced by one or more viral or non-viral promoter or promoter/enhancer elements (e.g., other retroviral LTRs and/or non-retroviral promoters or promoter/enhancers such as the CMV promoter/enhancer or the SV40 promoter) similar to the hybrid LTRs described by Chang, et al., *J. Virology* 67, 743-752, 1993; Finer, et al., *Blood* 83, 43-50, 1994 and Robinson, et al., *Gene Therapy* 2, 269-278, 1995.

The tRNA binding site and origin of second strand DNA synthesis are also important for a retrovirus to be biologically active, and may be readily identified by one of skill in the art. For example, tRNA binds to a retroviral tRNA binding site by Watson-Crick base pairing, and is carried with the retrovirus genome into a viral particle. The tRNA is then utilized as a primer for DNA synthesis by reverse transcriptase. The tRNA binding site may be readily identified based upon its location just downstream from the 5' LTR. Similarly, the origin of second strand DNA synthesis is, as its name implies, important for the second strand DNA synthesis of a retrovirus. This region, which is also referred to as the poly-purine tract, is located just upstream of the 3' LTR.

In addition to 5' and 3' LTRs, a tRNA binding site, a packaging signal, and an origin of second strand DNA synthesis, certain preferred recombinant retroviral vector constructs for use herein also comprise one or more genes of interest. In addition, the retroviral vectors may, but need not, include an RNA export element (also variously referred to as RNA transport, nuclear transport or nuclear export elements) that may be a RRE (Rev-responsive element) or a heterologous transport element. Representative examples of suitable heterologous RNA export elements include the Mason-Pfizer monkey virus constitutive transport element (Bray et al., *PNAS USA* 91, 1256-1260, 1994), the hepatitis B virus posttranscriptional regulatory element (Huang et al., *Mol Cell. Biol.* 73:7476-7486, 1993 and Huang et al., *J. Virology* 65:3193-3199, 1994), or lentiviral Rev-responsive elements (Daly et al., *Nature* 342:816-819, 1989 and Zapp et al., *Nature* 342:714-716, 1989).

Retroviral vector constructs that lack both gag/pol and env coding sequences may be used with the present disclosure. As utilized herein, the phrase "lacks gag/pol or env coding sequences" should be understood to mean that the vector contains less than 20, preferably less than 15, more preferably less than 10, and most preferably less than 8 consecutive nucleotides that are found in gag/pol or env genes, and in particular, within gag/pol or env expression cassettes that are used to construct packaging cell lines for the retroviral vector construct. This aspect of the present disclosure provides for retroviral vectors having a low probability of undesirable recombination with gag/pol or env sequences that may occur in a host cell or be introduced therein, for example, by transformation with an expression cassette. The production of retroviral vector constructs lacking gag/pol or env sequences may be accomplished by partially eliminating the packaging signal and/or the use of a modified or heterologous packaging signal. Within other embodiments of the present disclosure, retroviral vector constructs are provided wherein a portion of the packaging signal that may extend into, or overlap with, the retroviral gag/pol sequence is modified (e.g., deleted, truncated, or bases exchanged). Within other aspects of the present disclosure, retroviral vector constructs are provided that include the packaging signal that may extend beyond the start of the gag/pol gene. Within certain embodiments, the packaging signal that may extend beyond the start of the gag/pol gene is modified in order to contain one, two, or more stop codons within the gag/pol reading frame. Most preferably, one of the stop codons eliminates the gag/pol start site. In other embodiments, the introduced mutation may cause a frame shift in the gag/pol coding region.

Other retroviral gene delivery vehicles may likewise be utilized within the context of the present disclosure, including for example those described in EP 0,415,731; WO 90/07936; WO 91/0285, WO 9403622; WO 9325698; WO 9325234; U.S. Pat. No. 5,219,740; WO 9311230; WO 9310218; Vile and Hart, *Cancer Res.* 53:3860-3864, 1993; Vile and Hart, *Cancer Res.* 53:962-967, 1993; Ram et al., *Cancer Res.* 53:83-88, 1993; Takamiya et al., *J. Neurosci. Res.* 33:493-503, 1992; Baba et al., *J. Neurosurg.* 79:729-735, 1993 (U.S. Pat. No. 4,777,127, GB 2,200,651, EP 0,345,242 and WO91/02805).

Packaging cell lines suitable for use with the above described retroviral constructs may be readily prepared (see, e.g., U.S. Pat. Nos. 5,591,624 and 6,013,517; and International Publication No. WO 95/30763), and utilized to create producer cell lines for the production of recombinant vector particles. The parent cell line from which the packaging cell line is derived can be selected from a wide variety of mammalian cell lines, including for example, human cells, monkey cells, feline cells, dog cells, mouse cells, and the like.

After selection of a suitable host cell for the generation of a packaging cell line, one or more expression cassettes are introduced into the cell line in order to complement or supply in trans components of the vector which have been deleted (see, e.g., U.S. Pat. Nos. 5,591,624 and 6,013,517, incorporated herein by reference in their entireties; and International Publication No. WO 95/30763). For example, packaging expression cassettes may encode either gag/pol sequences alone, gag/pol sequences and one or more of vif, rev, or ORF 2, or one or more of vif, rev, or ORF 2 alone and may contain an RNA export element. For example, the packaging cell line may contain only ORF 2, vif, or rev alone, ORF 2 and vif, ORF 2 and rev, vif and rev, or all three of ORF 2, vif and, rev.

Packaging cell lines may also comprise a promoter and a sequence encoding ORF 2, vif, rev, or an envelope (e.g., VSV-G), wherein the promoter is operatively linked to the sequence encoding ORF 2, vif, rev, or the envelope. For packaging cell lines containing inducible gag/pol or env expression cassettes, additional expression cassettes facilitating the transactivation of the inducible promoter may be incorporated. The expression cassette may or may not be stably integrated. The packaging cell line, upon introduction of a retroviral vector, may produce particles at a concentration of greater than 103, 104, 105, 106, 107, 108, or 109 cfu/mL.

ii. Lentiviral Vectors

"Lentivirus" refers to a virus belonging to the lentivirus genus. Lentiviruses include, but are not limited to, human immunodeficiency virus (HIV) (for example, HIV-1 or HIV-2), simian immunodeficiency virus (SIV), feline immunodeficiency virus (FIV), Maedi-Visna-like virus (EV1), equine infectious anemia virus (EIAV) and caprine arthritis encephalitis virus (CAEV).

The terms "lentiviral vector construct," "lentiviral vector," and "recombinant lentiviral vector" are used interchangeably herein and refer to a nucleic acid construct derived from a lentivirus that carries and, within certain embodiments, is capable of directing the expression of a nucleic acid molecule of interest. Lentiviral vectors can have one or more of the lentiviral wild-type genes deleted in whole or part but retain functional flanking long-terminal repeat (LTR) sequences. The LTRs need not be the wild-type nucleotide sequences, and may be altered, e.g., by the insertion, deletion or substitution of nucleotides, so long as the sequences provide for functional rescue, replication, and packaging. The lentiviral vector may also contain a selectable marker.

The term "recombinant lentivirus" refers to a virus particle that contains a lentivirus-derived viral genome, lacks the self-renewal ability, and has the ability to introduce a nucleic acid molecule into a host. For example, the recombinant lentiviruses of the present disclosure include virus particles comprising a nucleic acid molecule that comprises a lentiviral genome-derived packaging signal sequence. The recombinant lentivirus is capable of reverse transcribing its genetic material into DNA and incorporating this genetic material into a host cell's DNA upon infection. Recombinant lentivirus particles may have a lentiviral envelope, a non-lentiviral envelope (e.g., an amphotropic or VSV-G envelope), a chimeric envelope, or a modified envelope (e.g., truncated envelopes or envelopes containing hybrid sequences).

A nucleic acid carried by a lentiviral vector of the present disclosure can be introduced into pluripotent stem cells or neural progenitor cells by contacting this vector with pluripotent stem cells of primates, including humans, or rodents, including mice and rats. The present disclosure relates to methods for introducing suicide genes into pluripotent stem cells, which comprise the step of contacting pluripotent stem cells with the vectors of the present disclosure. The pluripotent stem cells targeted for gene introduction are not particularly limited and, for example, include embryonic stem cells or induced pluripotent stem cells.

iii. Adenoviral Vector

The polynucleotide encoding a cell-cycle dependent promoter operatively linked to a suicide gene may be provided in an adenoviral vector. Although adenovirus vectors are known to have a low capacity for integration into genomic DNA, this feature is counterbalanced by the high efficiency of gene transfer afforded by these vectors. Adenovirus expression vectors include constructs containing adenovirus sequences sufficient to (a) support packaging of the construct and (b) to ultimately express a recombinant gene construct that has been cloned therein.

Adenovirus growth and manipulation is known to those of skill in the art, and exhibits broad host range in vitro and in vivo. This group of viruses can be obtained in high titers, e.g., 109-1011 plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus may be used as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNAs issued from this promoter possess a 5'-tripartite leader (TPL) sequence which makes them particular mRNA's for translation.

A recombinant adenovirus provided herein can be generated from homologous recombination between a shuttle vector and provirus vector. Due to the possible recombination between two proviral vectors, wild-type adenovirus may be generated from this process. Therefore, a single clone of virus is isolated from an individual plaque and its genomic structure is examined.

The adenovirus vector may be replication defective, or at least conditionally defective, the nature of the adenovirus vector is not believed to be crucial to the successful practice of the present disclosure. The adenovirus may be of any of the 42 different known serotypes or subgroups A-F. Adenovirus type 5 of subgroup C is the particular starting material in order to obtain the conditional replication-defective adenovirus vector for use in the present disclosure. This is because Adenovirus type 5 is a human adenovirus about which a great deal of biochemical and genetic information is known, and it has historically been used for most constructions employing adenovirus as a vector.

Nucleic acids can be introduced to adenoviral vectors as a position from which a coding sequence has been removed. For example, a replication defective adenoviral vector can have the E1-coding sequences removed. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Generation and propagation of replication deficient adenovirus vectors can be performed with helper cell lines. One unique helper cell line, designated 293, was transformed from human embryonic kidney cells by Ad5 DNA fragments and constitutively expresses E1 proteins (Graham et al., 1977). Since the E3 region is dispensable from the adenovirus genome (Jones and Shenk, 1978), adenovirus vectors, with the help of 293 cells, carry foreign DNA in either the E1, the E3, or both regions (Graham and Prevec, 1991).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, a particular helper cell line is 293.

Methods for producing recombinant adenovirus are known in the art, such as U.S. Pat. No. 6,740,320, incorporated herein by reference. Also, Racher et al. (1995) have disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) are employed as follows. A cell inoculum, resuspended in 5 ml of medium, is added to the carrier (50 ml) in a 250 ml Erlenmeyer flask and left stationary, with occasional agitation, for 1 to 4 hours. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 hours.

iv. Adeno-Associated Viral Vector

Adeno-associated virus (AAV) is may be used in the present disclosure as it has a high frequency of integration and it can infect nondividing cells, thus making it useful for delivery of genes into mammalian cells (Muzyczka, 1992). AAV has a broad host range for infectivity (Tratschin, et al., 1984; Laughlin, et al., 1986; Lebkowski, et al., 1988; McLaughlin, et al., 1988), which means it is applicable for use with the present disclosure. Details concerning the generation and use of rAAV vectors are described in U.S. Pat. Nos. 5,139,941 and 4,797,368.

AAV is a dependent parvovirus in that it requires coinfection with another virus (e.g., adenovirus or a member of the herpes virus family) to undergo a productive infection in cultured cells (Muzyczka, 1992). In the absence of coinfection with helper virus, the wild-type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is rescued from the chromosome or from a recombinant plasmid, and a normal productive infection is established (Samulski et al., 1989; McLaughlin et al., 1988; Kotin et al., 1990; Muzyczka, 1992).

A recombinant AAV (rAAV) virus may be made by cotransfecting a plasmid containing the gene of interest flanked by the two AAV terminal repeats (McLaughlin et al., 1988; Samulski et al., 1989; each incorporated herein by reference) and an expression plasmid containing the wild-type AAV coding sequences without the terminal repeats, for example pIM45 (McCarty et al., 1991). The cells can also be infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994; Clark et al., 1995). Cell lines carrying the rAAV DNA as an integrated provirus can also be used (Flotte et al., 1995).

v. Other Viral Vectors

Other viral vectors may be employed as constructs in the present disclosure. Vectors derived from viruses such as vaccinia virus (Ridgeway, 1988; Baichwal and Sugden, 1986; Coupar et al., 1988) and herpes simplex viruses may be employed. They offer several attractive features for various mammalian cells (Friedmann, 1989; Ridgeway, 1988; Baichwal and Sugden, 1986; Coupar et al., 1988; Horwich et al., 1990). In some embodiments, the polynucleotide may be delivered using integrating adenovectors.

A molecularly cloned strain of Venezuelan equine encephalitis (VEE) virus has been genetically refined as a replication competent vaccine vector for the expression of heterologous viral proteins (Davis et al., 1996). Studies have demonstrated that VEE infection stimulates potent CTL responses and has been suggested that VEE may be an extremely useful vector for immunizations (Caley et al., 1997).

In further embodiments, the polynucleotide is housed within an infective virus that has been engineered to express a specific binding ligand. The virus particle will thus bind specifically to the cognate receptors of the target cell and deliver the contents to the cell. Specific targeting of retrovirus vectors may be based on the chemical modification of a retrovirus by the chemical addition of lactose residues to the viral envelope. This modification can permit the specific infection of hepatocytes via sialoglycoprotein receptors.

For example, targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

2. Other Methods of Nucleic Acid Delivery

In addition to viral delivery of the polynucleotides comprising a cell cycle-dependent promoter operatively linked to a suicide gene, the following are additional methods of recombinant gene delivery to a given host cell and are thus considered in the present disclosure.

Introduction of a nucleic acid, such as DNA or RNA, may use any suitable methods for nucleic acid delivery for transformation of a cell, as described herein or as would be known to one of ordinary skill in the art. Such methods include, but are not limited to, direct delivery of DNA such as by injection of naked DNA, nanoparticles, such as lipid nanoparticles, gene gun, ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

i. Electroporation

In certain particular embodiments of the present disclosure, the gene construct is introduced into target cells via electroporation. Electroporation involves the exposure of cells (or tissues) and DNA (or a DNA complex) to a high-voltage electric discharge.

It is contemplated that electroporation conditions for hyperproliferative cells from different sources may be optimized. One may particularly wish to optimize such parameters as the voltage, the capacitance, the time and the electroporation media composition. The execution of other routine adjustments will be known to those of skill in the art. See e.g., Hoffman, 1999; Heller et al., 1996.

ii. Lipid-Mediated Transformation

In a further embodiment, the polynucleotide comprising a cell cycle-dependent promoter operatively linked to a suicide gene may be entrapped in a liposome or lipid formulation. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a gene construct complexed with Lipofectamine (Gibco BRL).

Lipid-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of lipid-mediated delivery and expression of foreign DNA in cultured chick embryo, HeLa and hepatoma cells.

Lipid based non-viral formulations provide an alternative to adenoviral gene therapies. Although many cell culture studies have documented lipid based non-viral gene transfer, systemic gene delivery via lipid based formulations has been limited. A major limitation of non-viral lipid based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in lipid vehicle stability in the presence and absence of serum proteins. The interaction between lipid vehicles and serum proteins has a dramatic impact on the stability characteristics of lipid vehicles (Yang and Huang, 1997). Cationic lipids attract and bind negatively charged serum proteins. Lipid vehicles associated with serum proteins are either dissolved or taken up by macrophages leading to their removal from circulation. Current in vivo lipid delivery methods use subcutaneous, intradermal, intratumoral, or intracranial injection to avoid the toxicity and stability problems associated with cationic lipids in the circulation. The interaction of lipid vehicles and plasma proteins is responsible for the disparity between the efficiency of in vitro (Felgner et al., 1987) and in vivo gene transfer (Zhu el al., 1993; Philip et al., 1993; Solodin et al., 1995; Liu et al., 1995; Thierry et al., 1995; Tsukamoto et al., 1995; Aksentijevich et al., 1996).

Advances in lipid formulations have improved the efficiency of gene transfer in vivo (Templeton et al. 1997; WO 98/07408). A novel lipid formulation composed of an equimolar ratio of 1,2-bis(oleoyloxy)-3-(trimethyl ammonio) propane (DOTAP) and cholesterol significantly enhances systemic in vivo gene transfer, approximately 150 fold. The DOTAP:cholesterol lipid formulation forms unique structure termed a "sandwich liposome". This formulation is reported to "sandwich" DNA between an invaginated bi-layer or 'vase' structure. Beneficial characteristics of these lipid structures include a positive p, colloidal stabilization by cholesterol, two dimensional DNA packing and increased serum stability. Patent Application Nos. 60/135,818 and 60/133,116 discuss formulations that may be used with the present disclosure.

The production of lipid formulations often is accomplished by sonication or serial extrusion of liposomal mixtures after (I) reverse phase evaporation (II) dehydration-rehydration (III) detergent dialysis and (IV) thin film hydration. Once manufactured, lipid structures can be used to encapsulate compounds that are toxic (chemotherapeutics) or labile (nucleic acids) when in circulation. Lipid encapsulation has resulted in a lower toxicity and a longer serum half-life for such compounds (Gabizon et al., 1990). Numerous disease treatments are using lipid based gene transfer strategies to enhance conventional or establish novel therapies, in particular therapies for treating hyperproliferative diseases.

iii. Cell-Permeating Peptides

The present disclosure contemplates fusing or conjugating a cell-penetrating peptide (also called a cell delivery domain, or cell transduction domain) to the polynucleotide comprising a cell cycle-dependent promoter operatively linked to a suicide gene. Such domains are well known in the art and are generally characterized as short amphipathic or cationic peptides and peptide derivatives, often containing multiple lysine and arginine resides (Fischer, 2007). Of particular interest are the TAT sequence from HIV1, and poly-D-Arg and poly-D-Lys sequences (e.g., dextrorotary residues, eight residues in length).

B. Regulatory Elements

Expression cassettes included in vectors useful in the present disclosure in particular contain (in a 5'-to-3' direction) a eukaryotic transcriptional promoter operably linked to a protein-coding sequence, splice signals including intervening sequences, and a transcriptional termination/polyadenylation sequence. The promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation. A promoter used in the context of the present disclosure includes a cell-cycle dependent promoter.

1. Promoter/Enhancers

In certain embodiments, the expression constructs provided herein comprise a cell-cycle dependent promoter to drive expression of the suicide gene. A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, through world wide web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

For cell replacement therapy using precursor cells, it is preferable that the gene is expressed under the control of a cell cycle-dependent promoter. Examples of cell cycle-dependent promoters include, but are not limited to those listed in Table 1. Cell cycle-dependent promoters may be derived from genes involved in the cell cycle, such as genes with expression in the G(2) phase and mitosis. Cell cycle-dependent promoters may comprise synthetic promoters. For cell replacement therapy, progenitors should generally maintain migratory potential and integrate appropriately into degenerating regions.

TABLE 1

Cell cycle-dependent promoters.

| Promoter | References |
| --- | --- |
| Ki-67 | Zambon A. C. *Cytometry A.* 77(6): 564-570, 2010. |
| PCNA | Whitfield et al., *Nature Reviews Cancer* 6: 99-106, 2006. |
| CKS2 | |
| TOP2A | |
| BUB1, BUB1B | |
| CHEK1 | |
| AURKA, AURKB | |
| TRIP, TRIP13 | |
| CDC7 | |
| ORC1L | |
| PRIM1 | |
| RFC1 | |
| RRM1, RRM2 | |
| FEN1 | |

TABLE 1-continued

Cell cycle-dependent promoters.

| Promoter | References |
|---|---|
| CCNA2, CCNB1, CCNE1, CCNF CDC20 DDX11 E2F3 PKMYT1 PLK1 TIMP1 CDC25C CENPF, CENPN MCM2, MCM3, MCM4, MCM5, MCM6, MCM7, MCM10 | |
| E2F | Dimova et al., Oncogene 24: 2810-2826, 2005. |
| SKP2 | Imaki et al., Cancer Res. 63(15): 4607-13, 2003. |
| CHR | Muller et al., Nucleic Acids Res. 40(4): 1561-1578, 2012. |
| SMC4 | Ren et al., Genes and Dev. 16: 245-256, 2002. |
| MELK | Fischer et al., Nucleic Acids Research 2015. |
| CKAP2 | Kang et al., Biochem Biophys Res Commun. 420(4): 822-7, 2012. |
| DBF4 | Wu X. and Lee H. Oncogene 21(51): 7786-96, 2002. |
| CDK4 | Pawar et al. Oncogene 23(36): 6125-35, 2004. |
| ZWILCH | Salvatore et al., Cancer Res. 67(21): 10148-10158, 2007. |
| POLE2 ZWINT GINS2 SMC4 HMMR NCAPH TTK PBK CEP55 | |
| ECT2 | Seguin et al., Molecular and Cellular Biology 29(2), 2009. |
| STIL | |
| FBXO5 | Balciunaite et al., Molecular and Cellular Biology 25(18), 2005. |
| SHCBP1 | Grant et al., Molecular Biology of the Cell 24(23): 3634-3650, 2013. |
| KIF23, KIF11, KIF4A DLGAP5 | |
| RRM2 | Zhang et al., Molecular Cancer 8(11), 2009. |
| CDCA7 | Gill et al., Molecular and Cellular Biology 33(3): 498-513, 2013. |
| HELLS | Mjelle et al., DNA Repair 30: 53-67, 2015. |
| SGOL2 | Llano et al., Genes Dev. 22(17): 2400-13, 2008. |
| KIAA0101/p15$^{PAF}$ | Chang et al., PLOS One 8(4): e61196, 2013. |
| NUF2 | Suzuki et al., Nature Cell Biology 18: 382-392, 2016. |
| NDC80 | |
| NUSAP1 | Yamamoto et al., Nucleic Acid Res. 2016. |
| DTL | Westendorp et al., Nucleic Acids Research 1-13, 2011. |
| MLF1IP | |
| ASPM | Wu et al., J Biol Chem. 3(43): 29396-29404, 2008. |

In certain aspects, methods of the disclosure also concern enhancer sequences, i.e., nucleic acid sequences that increase a promoter's activity and that have the potential to act in cis, and regardless of their orientation, even over relatively long distances (up to several kilobases away from the target promoter). However, enhancer function is not necessarily restricted to such long distances as they may also function in close proximity to a given promoter.

2. Initiation Signals and Linked Expression

A specific initiation signal also may be used in the expression constructs provided in the present disclosure for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

Additionally, certain 2A sequence elements could be used to create linked- or co-expression of genes in the constructs provided in the present disclosure. For example, cleavage sequences could be used to co-express genes by linking open reading frames to form a single cistron. An exemplary cleavage sequence is the F2A (Foot-and-mouth disease virus 2A) or a "2A-like" sequence (e.g., Thosea asigna virus 2A; T2A) (Minskaia and Ryan, 2013).

3. Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in programming, which is a specific nucleic acid sequence at which replication is initiated. Alternatively a replication origin of other extra-chromosomally replicating virus as described above or an autonomously replicating sequence (ARS) can be employed.

4. Selection and Screenable Markers

In some embodiments, cells containing a construct of the present disclosure may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art.

C. Suicide Genes and Prodrugs

In some embodiments, a suicide gene is a nucleic acid which, upon administration of a prodrug, effects transition of a gene product to a compound which kills its host cell. Examples of suicide gene/prodrug combinations which may be used are cytomegalovirus (CMV)-UL97, Herpes Simplex Virus-thymidine kinase (HSV-tk) and ganciclovir, acyclovir, or FIAU; oxidoreductase and cycloheximide; cytosine deaminase and 5-fluorocytosine; thymidine kinase thymidilate kinase (Tdk::Tmk) and AZT; and deoxycytidine kinase and cytosine arabinoside. The E. coli purine nucleoside phosphorylase which converts the prodrug 6-methylpurine deoxyriboside to toxic purine 6-methylpurine may also be used.

In some embodiments, the HSV thymidine kinase (TK) or CMV-UL97 suicide gene may have one or more mutations from the wild-type or unmutated HSV TK or CMV-UL97. As utilized herein, it should be understood that "unmutated thymidine kinase" refers to native or wild-type thymidine kinase such as that described by McKnight et al. (Nucl. Acids Res. 8:5949-5964, 1980). The TK mutants can have one or more amino acid substitutions at residues 159-161 and 168-169 of HSV TK (Black et al., Proc. Nat'l Acad. USA 93:3525-3529, 1996). The TK mutant used in the present methods may be SR11, SR26, SR39, SR4, SR15, SR32, or SR53 TK mutants. For example, the HSV TK can be HSV1-SR39TK (i.e, $_{159}$IFL$_{161}$ and $_{168}$FM$_{169}$, amino acid substitution at position 159 is leucine to isoleucine, at position 160 is isoleucine to phenylalanine, at position 161 is phenylalanine to leucine, at position 168 is alanine to phenylalanine, and at position 169 is leucine to methionine) which has an enhanced ability to convert the prodrug acyclovir and/or ganciclovir into cytotoxic agents (U.S. Patent Publication Nos. 20130011903 and 20120142071; incorporated herein by reference in their entirety).

The mutations may be upstream or downstream of the DRH nucleoside binding site. For example, mutations which encode one or more amino acid substitutions from 1 to 7 amino acids upstream from the DRH nucleoside binding site are contemplated. The biological activity of such kinases may be readily determined utilizing any of the assays which are described herein, including for example, determination of the rate of nucleoside analogue uptake, determination of the rate of nucleoside or nucleoside analogue phosphorylation. In addition, thymidine kinase mutants may be readily selected which are characterized by other biological properties, such as thermostability, and protein stability (e.g., described in U.S. Pat. No. 6,451,571).

Briefly, thymidine kinase mutants of the present disclosure may be prepared from a wide variety of Herpesviridae thymidine kinases, including for example both primate herpesviruses, and nonprimate herpesviruses such as avian herpesviruses. Representative examples of suitable herpesviruses include Herpes Simplex Virus Type 1 (McKnight et al., Nuc. Acids Res 8:5949-5964, 1980), Herpes Simplex Virus Type 2 (Swain and Galloway, J. Virol. 46:1045-1050, 1983), Varicella Zoster Virus (Davison and Scott, J. Gen. Virol. 67:1759-1816, 1986), marmoset herpesvirus (Otsuka and Kit, Virology 135:316-330, 1984), feline herpesvirus type 1 (Nunberg et al., J. Virol. 63:3240-3249, 1989), pseudorabies virus (Kit and Kit, U.S. Pat. No. 4,514,497, 1985), equine herpesvirus type 1 (Robertson and Whalley, Nuc. Acids Res. 16:11303-11317, 1988), bovine herpesvirus type 1 (Mittal and Field, J. Virol 70:2901-2918, 1989), turkey herpesvirus (Martin et al., J. Virol. 63:2847-2852, 1989), Marek's disease virus (Scott et al., J. Gen. Virol. 70:3055-3065, 1989), herpesvirus saimiri (Honess et al., J. Gen. Virol. 70:3003-3013, 1989) and Epstein-Barr virus (Baer et al., Nature (London) 310:207-311, 1984).

Such herpesviruses may be readily obtained from commercial sources such as the American Type Culture Collection ("ATCC", Rockville, Md.). Deposits of certain of the above-identified herpesviruses may be readily obtained from the ATCC, for example: ATCC No. VR-539 (Herpes simplex type 1); ATCC Nos. VR-734 and VR-540 (Herpes Simplex type 2); ATCC No. VR-586 (Varicella Zoster Virus); ATCC No. VR-783 (Infectious laryngothracheitis); ATCC Nos. VR-624 VR-987, VR-2103, VR-2001, VR-2002, VR-2175, VR-585 (Marek's disease virus); ATCC Nos. VR-584B and VR-584B (turkey herpesvirus); ATCC Nos. VR-631 and VR-842 (bovine herpesvirus type 1); and ATCC Nos. VR-2003, VR-2229 and VR-700 (equine herpesvirus type 1). Herpesviruses may also be readily isolated and identified from naturally occurring sources (e.g., from an infected animal).

Thymidine kinase mutants used in the present disclosure may be constructed using a wide variety of techniques. For example, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, oligonucleotide-directed site-specific (or segment specific) mutagenesis procedures may be employed to provide an altered gene having particular codons altered according to the substitution, deletion, or insertion required. Deletion or truncation derivatives of thymidine kinase mutants may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al. (Molecular cloning: A Laboratory Manual, 2d Ed., Cold Spring Harbor Laboratory Press, 1989).

Thymidine kinase mutants may also be constructed utilizing techniques of PCR mutagenesis, chemical mutagenesis (Drinkwater and Klinedinst, PNAS 83:3402-3406, 1986), by forced nucleotide misincorporation (e.g., Liao and Wise Gene 88:107-111, 1990), or by use of randomly mutagenized oligonucleotides (Horwitz et al., Genome 3:112-117, 1989).

In some embodiments, the suicide gene is the CMV-UL97 gene or a variant thereof. The prodrug may be ganciclovir, acyclovir, or penciclovir.

TABLE 2

Suicide Genes and Prodrugs (Denny et al., Biomedicine Biotechnol. 1: 48-70, 2003).

| Suicide Gene | Prodrug |
|---|---|
| HSV thymidine kinase (TK) | Ganciclovir (GCV) |
| | Ganciclovir elaidic acid ester |
| | Penciclovir (PCV) |
| | Acyclovir (ACV) |

TABLE 2-continued

Suicide Genes and Prodrugs (Denny et al., *Biomedicine Biotechnol.* 1: 48-70, 2003).

| Suicide Gene | Prodrug |
| --- | --- |
|  | Valacyclovir (VCV) |
|  | (E)-5-(2-bromovinyl)-2'-deoxyuridine (BVDU) |
|  | Zidovuline (AZT) |
|  | 2'-exo-methanocarbathymidine (MCT) |
| Cytosine Deaminase (CD) | 5-fluorocytosine (5-FC) |
| Purine nucleoside phosphorylase (PNP) | 6-methylpurine deoxyriboside (MEP) fludarabine (FAMP) |
| Cytochrome p450 enzymes (CYP) | Cyclophosphamide (CPA) Ifosfamide (IFO) 4-ipomeanol (4-IM) |
| Carboxypeptidases (CP) | 4-[(2-chloroethyl)(2-mesyloxyethyl)amino]benzoyl-L-glutamic acid (CMDA) Hydroxy- and amino-aniline mustards Anthracycline glutamates Methotrexate α-peptides (MTX-Phe) |
| Caspase-9 | AP1903 (Di Stasi et al., 2011) |
| Carboxylesterase (CE) | Irinotecan (IRT) Anthracycline acetals |
| Nitroreductase (NTR) | dinitroaziridinylbenzamide CB1954 dinitrobenzamide mustard SN23862 4-Nitrobenzyl carbamates Quinones |
| Horse radish peroxidase (HRP) | Indole-3-acetic acid (IAA) 5-Fluoroindole-3-acetic acid (FIAA) |
| Guanine Ribosyltransferase (XGRTP) | 6-Thioxanthine (6-TX) |
| Glycosidase enzymes | HM1826 Anthracycline acetals |
| Methionine-α,γ-lyase (MET) | Selenomethionine (SeMET) |
| Thymidine phosphorylase (TP) | 5'-Deoxy-5-fluorouridine (5'-DFU) |

IV. METHODS OF USE

PSCs to which genes have been introduced by vectors of the present disclosure (e.g., pseudotyped lentiviral vectors), and cells, tissues, organs and such differentiated from these PSCs are useful for assaying and screening for various types of pharmaceutical agents. Through gene transfer into PSCs, for example, pharmaceutical agents or genes for carrying out specific differentiation of tissues or cells, and particularly preferably tissues or cells derived from primates, can be evaluated for their effects or screened for.

The present disclosure also encompasses PSCs into which vectors of the present disclosure (e.g., pseudotyped lentiviral vectors) have been introduced, and differentiated cells and tissues that have differentiated from the PSCs. The differentiated cells and tissues can be identified based on marker expression and morphological characteristics specific to the tissues or cells.

A. Methods of Treatment

In some embodiments, the present disclosure provides methods of treating a disease or disorder in a subject comprising administering a population of precursor cells which comprise a suicide gene under the control of a cell cycle-dependent promoter. The precursor cells may be used to replace cells which are essentially non-dividing cells and any remaining cycling or proliferating cells may be eliminated by the administration of a pro-drug which is selectively kills these cycling cells. Thus, the method can prevent the formation of teratomas or tumors from the remaining cycling cells.

The treatment methods may be applied to any disease or disorder which may benefit from the replacement of a certain cell population. For example, neuronal diseases may be treated by the administration of precursor cells. Disease which affect the vasculature, such as tumor angiogenesis, may be treated by the administration of endothelial precursor cells. Cardiomyocyte precursor cells may be used in the treatment of heart diseases and pancreatic precursor cells may be used for the treatment of pancreatic diseases. Other precursor cell therapies of the present disclosure may comprise, but are not limited to, kidney precursor cells, oligodendrocyte precursor cells, hematopoietic precursor cells, myeloid precursor cells, mesenchymal precursor cells, retinal precursor cells, and osteoclast precursor cells.

In humans, there are numerous diseases affecting the CNS, many of which result in cerebellar degeneration with concomitant symptoms, such as dysmetria, ataxia, past pointing, dysdiadochokinesia, dysarthria, intention and action tremor, cerebellar nystagmus, rebound, hypotonia, and loss of equilibrium. These diseases may be alleviated using cell replacement therapy according to the specific embodiment disclosed herein.

Diseases of the CNS and brain in humans that are amenable to treatment using the methods of the present disclosure include a wide variety of diseases and disorders, including for example, Huntington's disease; Alzheimer's disease (both sporadic and familial); Parkinson's disease and Parkinson's disease-like symptoms, such as muscle tremors, muscle weakness, rigidity, bradykinesia, alterations in posture and equilibrium, and dementia; amyotrophic lateral sclerosis (ALS); spinal cord injury; severe epilepsy; traumatic brain injury; and the like.

Accordingly, the methods of the present disclosure may be used to alleviate abnormalities of the CNS and cerebellum that result in demyelination, dysmyelination, dementia, dysmetria, ataxia, past pointing, dysdiadochokinesia, dysarthria, intention and action tremor, cerebellar nystagmus, rebound, hypotonia, and loss of equilibrium. It is well established that patients with Parkinson's suffer from progressively disabled motor control due to loss of dopaminergic neurons within the basal ganglia, which innervate the striatum. Neural precursor cells can be directed toward a dopaminergic fate and delivered into the striatum using the systems described herein to prevent overgrowth and tumor formation. Likewise, neural precursors of the present disclosure can be directed toward a cholinergic fate for use in the treatment of Alzheimer's disease.

The methods of the present disclosure also have use in the veterinary field including treatment of domestic pets and farm animals. As utilized herein, the terms "treated, prevented, or, inhibited" refer to the alteration of a disease course or progress in a statistically significant manner. Determination of whether a disease course has been altered may be readily assessed in a variety of model systems and by using standard assays, known in the art, which analyze the ability of a gene delivery vector to delay or prevent CNS or cerebellar degeneration.

Gene delivery vectors may be delivered directly to the CNS or brain by injection into, e.g., a ventricle, a cerebellar lobule and/or the striatum, using a needle, catheter or related device. In particular, within certain embodiments of the present disclosure, one or more dosages may be administered directly in the indicated manner at dosages greater than or equal to $10^3$, $10^4$, $10^5$, $10^6$, $10^7$, $10^8$, $10^9$, $10^{10}$ or $10^{11}$ cfu. Cerebellar injections are complicated by the fact that stereotaxic coordinates cannot be used to precisely target the site of an injection; there is animal to animal variation in the size of cerebellar lobules, as well as their absolute three-dimensional orientation. Thus, cholera toxin subunit b (CTb) may be used to determine the exact location of the injection and reveal the pool of transducable neurons at an injection site. Injections may fill the molecular layer, Purkinje cell layer, granule cell layer and white matter of the arbor vitae but do not extend to the deep cerebellar nuclei.

Alternatively, and preferably for treating diseases using transduced neural progenitor cells, neural progenitor cells are first transduced ex vivo and then delivered to the CNS. Generally, if transduced ex vivo, cells will be infected with the viral vectors described herein at an MOI of about 0.01 to about 50, preferably about 0.05 to about 30, and most preferably about 0.1 to about 20 MOI. For FIV vectors, an MOI of about 0.05 to about 10, preferably about 0.1 to about 5, or even 0.1 to about 1, should be sufficient. Once transfected ex vivo, cells can be delivered, for example, to the ventricular region, as well as to the striatum, spinal cord and neuromuscular junction, using neurosurgical techniques known in the art, and as described in the examples below, such as by stereotactic injection and injections into the eyes and ears (see, e.g., Stein et al., *J Virol* 73:3424-3429, 1999; Davidson et al., *PNAS* 97:3428-3432, 2000; Davidson et al., *Nat. Genet.* 3:219-223, 1993; and Alisky and Davidson, *Hum. Gene Ther.* 77:2315-2329, 2000). In general, the amount of transduced cells in the compositions to be delivered to the subject will be from about 101 to about 1010 cells or more, more preferably about 101 to 108 cells or more, and even more preferably about 102 to about 104 cells, or more. Other effective dosages can be readily established by one of ordinary skill in the art through routine trials establishing dose response curves.

A wide variety of assays may be utilized in order to determine appropriate dosages for administration, or to assess the ability of a gene delivery vector to treat or prevent a particular disease. Certain of these assays are discussed in more detail below. For example, the ability of particular vectors to transduce cerebellar neurons and neural progenitor cells can be assessed using reporter genes, as discussed below. The ability of the transduced progenitor cells to differentiate may be tested, for example, using immunocytochemistry, as discussed below in the examples.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. The therapy may be repeated intermittently while symptoms detectable or even when they are not detectable. The therapy may be provided alone or in combination with other drugs.

Initial dosages can also be estimated from in vivo data, e.g., animal models, using techniques that are well known in the art. One having ordinary skill in the art could readily optimize administration to humans based on animal data.

B. Pharmaceutical Preparations

Where clinical application of a composition containing a therapeutic cell population of the present disclosure is undertaken, it will generally be beneficial to prepare a pharmaceutical composition appropriate for the intended application. This will typically entail preparing a pharmaceutical composition that is essentially free of pyrogens, as well as any other impurities that could be harmful to humans or animals.

The phrases "pharmaceutical or pharmacologically acceptable" refers to molecular entities and compositions that do not produce an adverse, allergic or other untoward reaction when administered to an animal, such as a human, as appropriate. The preparation of a pharmaceutical composition comprising a inhibitory nucleic acid or additional active ingredient will be known to those of skill in the art in light of the present disclosure, as exemplified by Remington (2005), incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. A pharmaceutically acceptable carrier is particularly formulated for administration to a human, although in certain embodiments it may be desirable to use a pharmaceutically acceptable carrier that is formulated for administration to a non-human animal but which would not be acceptable (e.g., due to governmental regulations) for administration to a human. Except insofar as any conventional carrier is incompatible with the active ingredient, its use in the therapeutic or pharmaceutical compositions is contemplated.

The present therapies of the embodiments can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art The actual dosage amount of a composition of the present disclosure administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject. In non-limiting examples, a dose may comprise from about 5 microgram/kg/body weight to about 500 milligram/kg/body weight, about 5 mg/kg/body weight to about 100 mg/kg/body weight, about 10 mg/kg/body weight to about 50 mg/kg/body weight, can be administered.

V. EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Example 1—Targeting of Proliferative Cells

Generation of TK-PSC Line:

The aim of this study was to develop a suicide gene approach towards the prevention of uncontrolled overgrowth of PSC-derived transplanted neural cells. For many reasons, ganciclovir and herpes simplex thymidine kinase is an attractive system for such a suicide gene technology. Indeed, ganciclovir is widely used in patients and penetrates into the central nervous system. However, constitutive expression of HSV-TK would not be desirable, as this could lead to immune rejection of transplanted cells, and the use of ganciclovir could potentially lead to killing of functional transplanted neurons.

Accordingly, HSV-TK was expressed under the control of a cell cycle-dependent Ki67 promoter fragment. For this purpose the human pluripotent ESC (hPSC) line HS415 was transduced with a lentivector coding for the expression of HSV-TK under the control of the Ki67 promoter fragment (Zambon, 2010). As the lentivector transduction efficiency of hPSC is in the range of 10-20%, a tool for selection of transduced cells was required. Thus, the construct that was used had the HSV-TK sequence fused to a zeocin resistance sequence. HSV-TK-positive cells were selected by culturing transduced hESC in the presence of zeocin (FIG. 1A). A polyclonal HSV-TK-expressing PSC line was obtained, referred to herein as TK-PSC. Neural precursor cells and mature neurons were obtained from TK-PSC and are to as TK-NPC and TK-neurons, respectively (FIG. 1B, 1C).

Highly Proliferative Cells Expressing Ki67/TK are Sensitive to Ganciclovir In Vitro:

Next, TK expression was investigated in TK-PSC and in TK neurons. In TK-PSC, virtually 100% of cells expressed TK in concordance with high expression of Ki67 in these cells (FIG. 1C, upper panel). In contrast, TK neurons did not express any TK, as predicted from them being post-mitotic cells. However, there were still Ki67-positive cells in the neuronal preparation (FIG. 1C, lower panel). These Ki67-positive cells likely do not reflect the presence of proliferating cells as many of the Ki67-positive cells in the neuronal preparation clearly showed a morphology of mature neurons with long neurite extension. The expression of Ki67 was also investigated, together with expression of the pluripotency markers nanog and oct3/4 by flow cytometry. In PSCs, virtually all cells were Ki67-, nanog-, and oct3/4-positive. In contrast, NPCs rapidly lost pluripotency markers after 1 week of neurosphere differentiation, while Ki67 expression decreased more slowly with levels slightly above background after 3 weeks of differentiation (FIG. 2A).

Figures 2A, 2B, 2C, 2D:
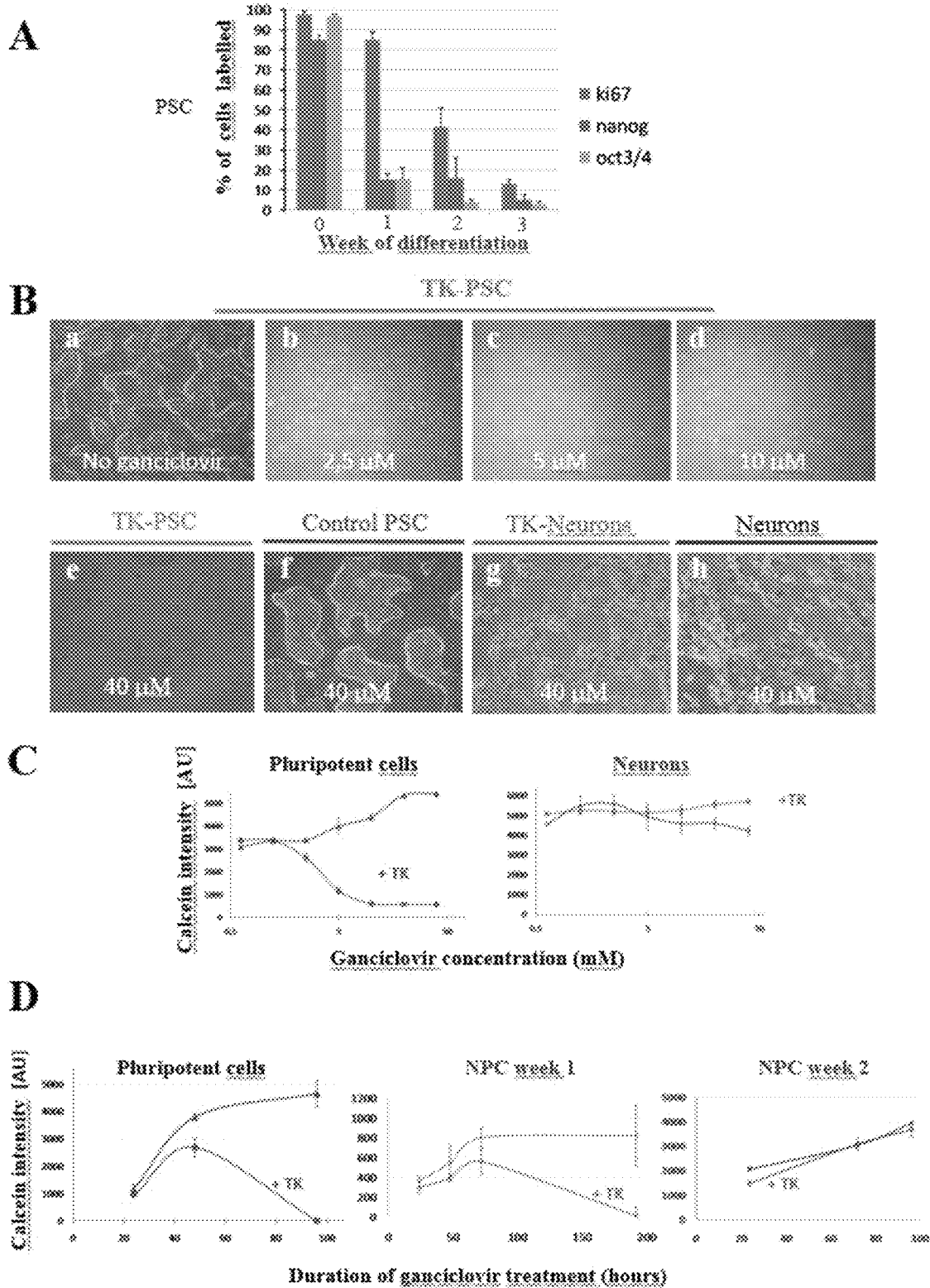
FIGS. 2A-2D: Effect of ganciclovir treatment in vitro. (A) Analysis of expression of proliferation markers (Ki67) and pluripotency markers (nanog, oct3/4) at different stages of the differentiation protocol described in FIG. 1B. Protein expression was analyzed by flow cytometry (mean+/−SEM of 4 independent experiments). (B) a-d: Undifferentiated pluripotent TK-PSC cells were exposed to increasing concentrations of ganciclovir (0, 2.5, 5, and 10 µM). (B) e-f: comparison of the effect of 40 µM ganciclovir on TK-expressing and control PSC. Note that in control PSC, no ganciclovir toxicity is observed even with the highest concentration of ganciclovir (40 µM). Upon neuronal differentiation, TK-expressing cells lose their sensitivity to ganciclovir as predicted by the lack of Ki67-driven TK expression in post-mitotic neurons (see FIG. 1C). (C) Dose response to ganciclovir: TK-PSC, control PSC; TK-neurons, and control neurons were exposed to increasing concentrations of ganciclovir. Cell viability was monitored using calcein. The control PSCs had higher expression of Calcein as compared to the TK-PSCs at increasing concentrations of ganciclovir. (D) Ganciclovir time course: TK and control PSC, 1 week NPC (TK and control), and 2 week NPC (TK and control) were exposed to 40 µM ganciclovir and cell toxicity was monitored using calcein. Data from panel C and D are shown as triplicate determinations and are representative of 3 independent experiments. Error bars=+/−SD, n=3.

The impact of ganciclovir on TK cells was determined in vitro (FIG. 2B, 2C, 2D). TK PSCs were highly sensitive to ganciclovir exposure (96h) and even at ganciclovir concentrations of 2.5 µM loss of cells was observed, which was almost complete at 10 µM (FIG. 2B, 2C). In contrast, regular PSCs (i.e., not transduced with the TK construct) were resistant to ganciclovir even at concentrations of 40 µM (FIG. 2B, 2F). As expected from the lack of TK expression in TK neurons, TK neurons were not affected by ganciclovir concentrations up to 40 µM, similar to the control neurons.

The time course of the ganciclovir effect was also investigated (FIG. 2D). TK PSCs were killed by Ganciclovir (40 µM) within 4 days. TK-NPCs after 1 week of neurosphere differentiation were still sensitive to Ganciclovir (40 µM), however the time course of killing was markedly slowed down and complete killing was observed only after 8 days. TK-NPCs after 2 weeks of neurosphere differentiation showed only little cell growth and were not killed by ganciclovir.

Figure 4A:
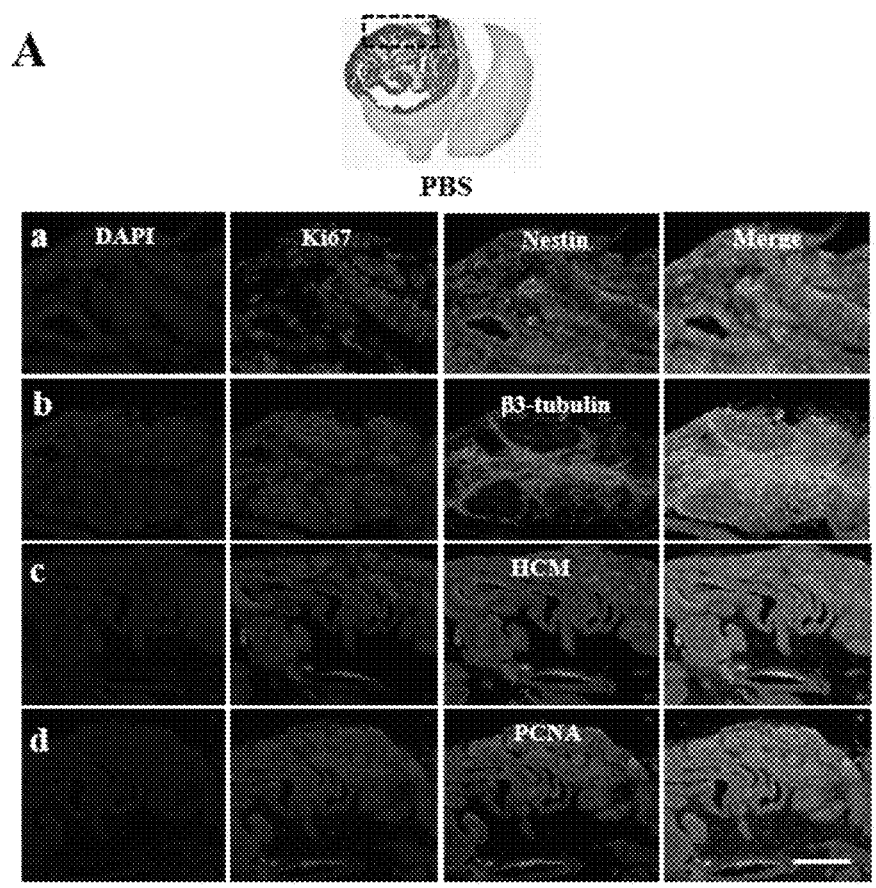
FIGS. 4A-4B: Early ganciclovir treatment prevents tumor formation after transplantation of HSV-TK-expressing pluripotent cells. (A) Transplantation of TK-PSC without ganciclovir treatment: teratoma formation was consistently observed after transplantation of TK-PSC into PBS-treated mice top panel: cresyl violet coloration; a-d lower panels: immunostaining of the graft (HCM staining allows detection of human typical proteins) show a development mainly towards neural tissue with expression of nestin (for immature neural cells), beta III tubulin (for mature neurons). Proliferative cells are stained with Ki67 and PCNA. (B) Transplantation of TK-PSC with early ganciclovir treatment: absence of teratoma formation and cell proliferation in mice transplanted with TK-PSC followed by early ganciclovir treatment (day 4 to 19 following transplantation); a-d top panel: cresyl violet coloration; e-f lower panels: immunostaining with HCM, Ki67 and PCNA. Mice were sacrificed and immunohistochemistry was performed one month after termination of ganciclovir treatment. Stainings shown in this figure are representative of 3-5 mice per group. Cells stained positive for Ki67 and HCM or PCNA; the staining overlaps in the merged images.
Figure 4B:
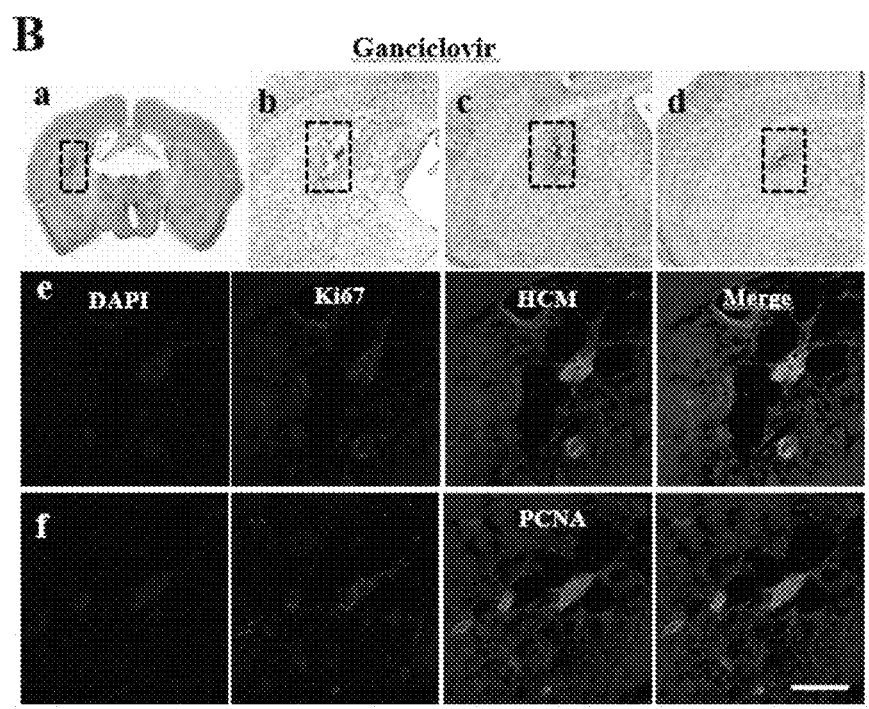
Figure 5A:
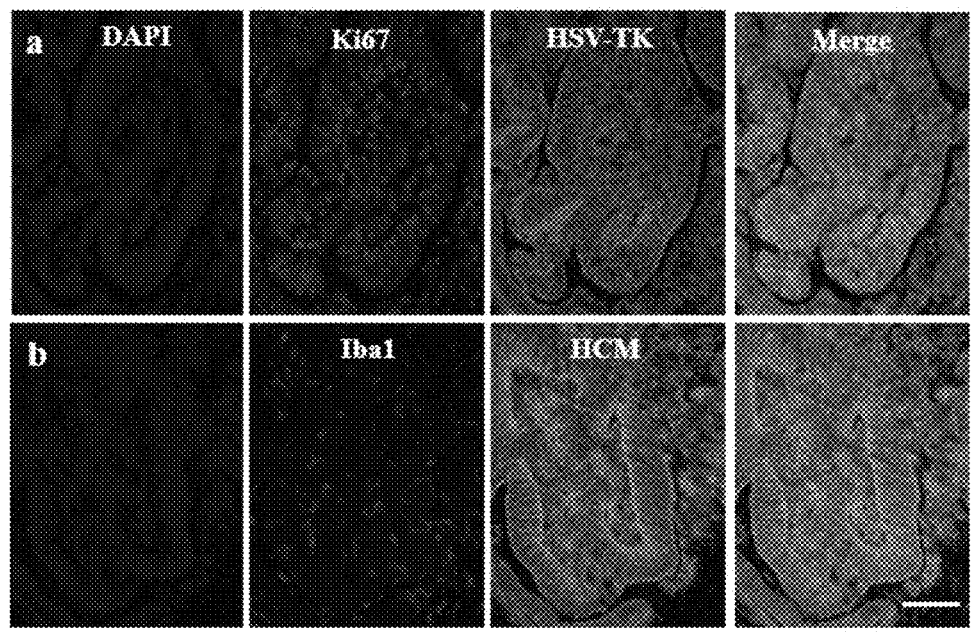
FIGS. 5A-5B: Early ganciclovir treatment and impact on Iba1 and Ki67-positive cells. (A) In the absence of ganciclovir treatment, there were abundant HSV-TK-containing, proliferating (Ki67), human (HCM) tumor cells; the tumors were infiltrated by microglia (Iba1). (B) In ganciclovir-treated mice, a human cell graft (HCM) was barely detectable and virtually no Ki67 and TK expression was observed in the graft region. Some microglia staining by Iba1 was detectable around the scar of the graft. Mice were sacrificed and immunohistochemistry was performed one month after termination of ganciclovir treatment.
Figure 5B:
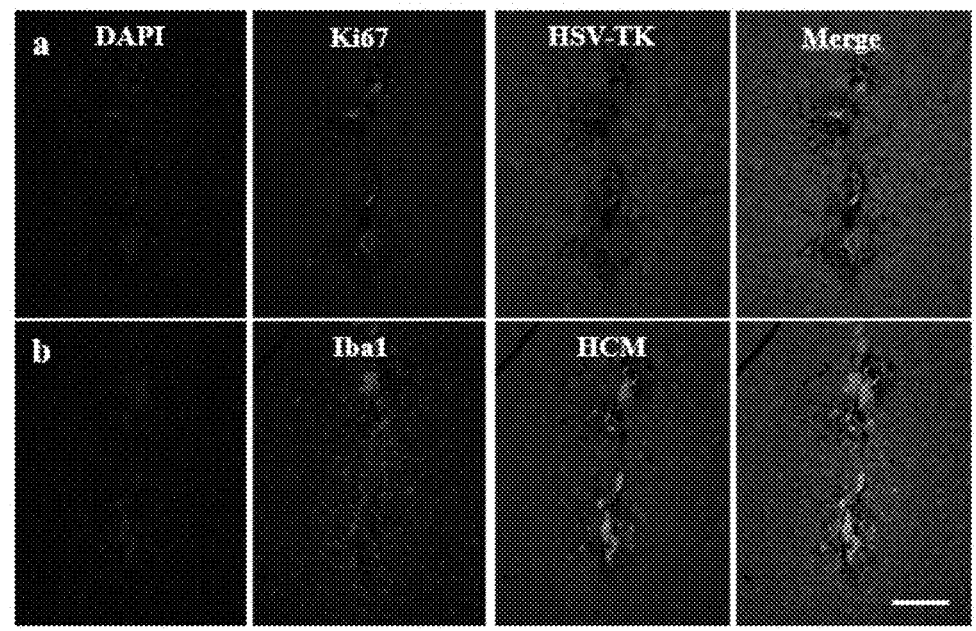

Early, but not Late Ganciclovir Treatment Prevents Tumor Formation Upon Transplantation of Highly Proliferative Pluripotent Stem Cells:

Given the encouraging results in vitro, it was investigated whether ganciclovir could prevent tumor formation in vivo. For this purpose, TK-PSC were transplanted into the striatum of NOD/SCID mice. In the absence of ganciclovir, mice, sacrificed 49 days post transplantation, consistently developed teratomas (FIG. 4A), which consisted of human cells (HCM-positive) and showed abundant expression of Ki67 and Ki67 promoter-driven HSV-TK (FIG. 5Aa). There was a moderate amount of mouse microglia invasion. In contrast, mice that were treated for 15 days with ganciclovir (starting 4 days post-transplantation) had no observed teratomas (FIG. 4B). There were hardly any human cells left in the ganciclovir-treated animals, and the few surviving human cells were negative for HSV-TK and—to a large extent—also negative for Ki67, suggesting that the few surviving human cells had become post-mitotic and therefore lost sensitivity to ganciclovir (FIG. 5Ba). Thus, ganciclovir prevented teratoma formation by transplanted TK-PSC.

Figure 6A:
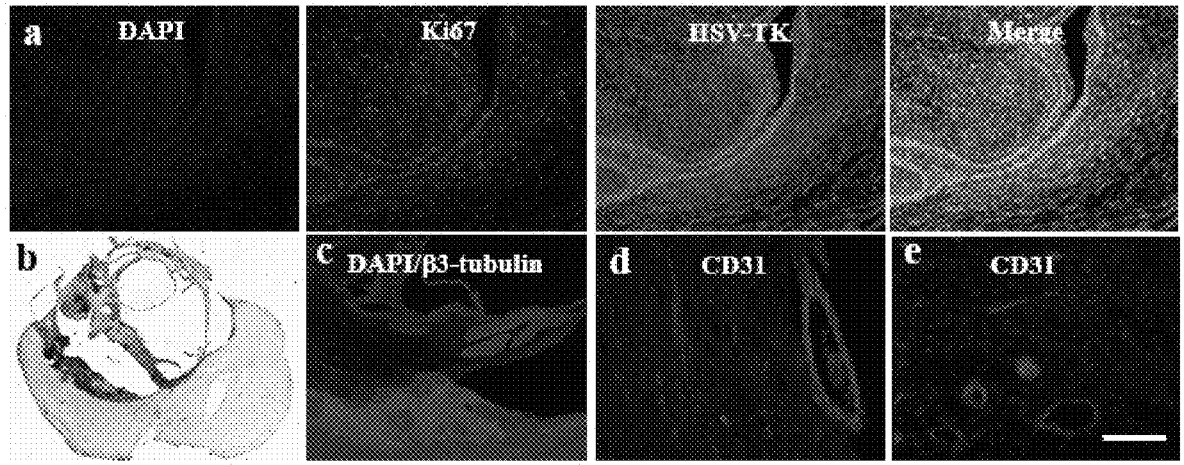
FIGS. 6A-6B: Late ganciclovir treatment does not prevent tumor formation after transplantation of HSV-TK-expressing pluripotent cells. Mice were transplanted with TK-PSC and PBS-treatment (A) or ganciclovir-treatment (B) was initiated one month after transplantation. Treatment was maintained for 15 days, followed by 1 month without treatment before sacrifice. Under these conditions, there was no difference between PBS-treated and ganciclovir-treated mice. The grafts have developed towards a tumor with predominantly neural tissue (beta III tubulin staining). Tumor cells expressed Ki67 and TK, but no Oct3/4. The grafts were vascularized, as evidenced by CD31 staining for endothelial cells.
Figure 6B:
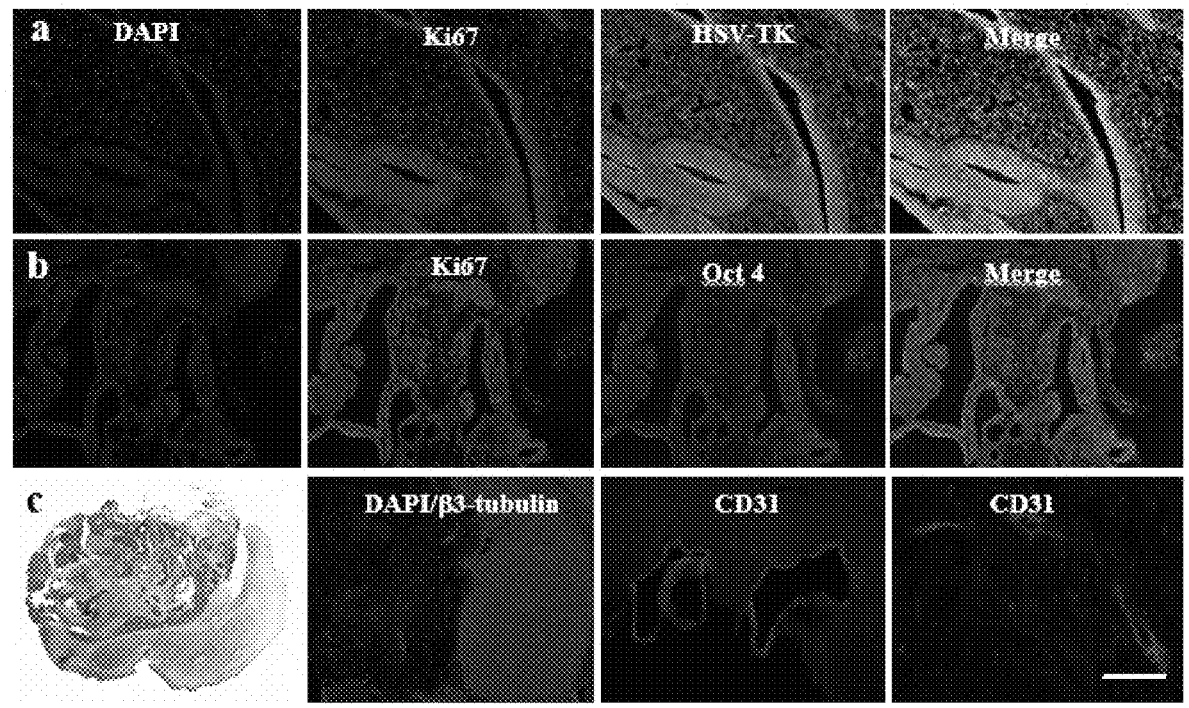

It was next investigated whether ganciclovir could also be used to treat already established teratomas. Therefore, teratoma formation was allowed to progress for 30 days (preliminary results had shown that within this time delay there was consistent teratoma formation upon transplantation of PSC) and treated with ganciclovir (or PBS) for days 30-45 post-transplantation. Mice were sacrificed 30 days after the end of the ganciclovir treatment. Under these conditions, there was teratoma formation in both, the PBS and the ganciclovir-treated animals (FIG. 6). CD31 staining showed that tumors were vascularized, suggesting that lack of perfusion did not account for the absence of a ganciclovir therapeutic effect in established tumors. Similarly, many teratoma cells showed high level expression of HSV-TK suggesting that down-regulation of the transgene was not the explanation for the lack of a therapeutic response.

Figures 7A, 7B, 7C:
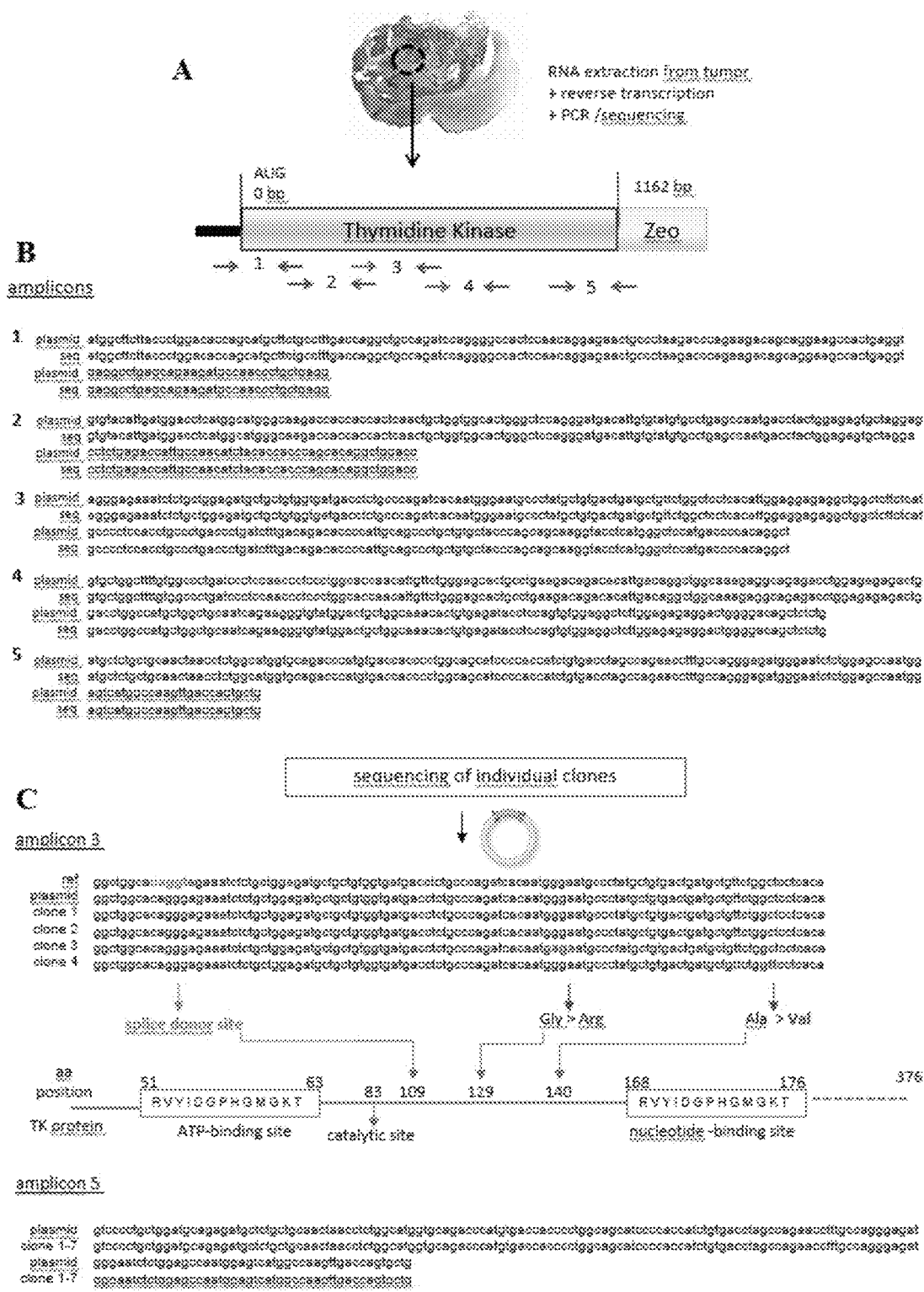
FIGS. 7A-7C: Sequencing of HSV-TK in pluripotent stem cell-derived tumors subjected to late ganciclovir treatment. (A) 2 weeks ganciclovir treatment was initiated 4 weeks after intrastriatal transplantation of pluripotent stem cells and mice were sacrificed 4 weeks after termination of treatment (as described in FIG. 6). DNA was extracted from PFA-fixed, paraffin-embedded tumor samples and amplified using the indicated PCR primers. (B) Direct sequencing of plasmid DNA and amplified sequences from tumor samples did not detect any mutations. (Amplicon 1—plasmid=SEQ ID NO: 11; "seq"=SEQ ID NO: 12; Amplicon 2—plasmid=SEQ ID NO: 13; "seq"=SEQ ID NO: 14; Amplicon 3—plasmid=SEQ ID NO: 15; "seq"=SEQ ID NO: 16; Amplicon 4—plasmid=SEQ ID NO: 17; "seq"=SEQ ID NO: 18; Amplicon 5—plasmid=SEQ ID NO: 19; "seq"=SEQ ID NO: 20) (C) Sequencing of HSV-TK subclones from amplicon 3 and 5 (derived from PCR reactions described for panel B). amplicon 3: plasmid DNA used for cell transduction, as well as tumor-derived cDNA clones did not contain the splice donor site found in the HSV-TK reference sequence. However, cDNA clones 3 and 4 showed coding non-synonymous mutations. (ref=SEQ ID NO: 21; plasmid=SEQ ID NO: 22; clone 1=SEQ ID NO: 23; clone 2=SEQ ID NO: 24; clone 3=SEQ ID NO: 25; clone 4=SEQ ID NO: 26; ATP-binding site=SEQ ID NO: 27; nucleotide-binding site=SEQ ID NO: 28) amplicon5: none of the cDNA clones showed any mutations. (plasmid=SEQ ID NO: 29; clone 1-7=SEQ ID NO: 30)

A previous study (Chalmers et al., 2001) had suggested that alternative splicing, due to cryptic splice donor and acceptor sites, can lead to formation of an inactive TK. Another study (Kotini et al., 2016) had suggested that various non-sense mutations may occur in the TK sequence in rapidly growing cells and might explain ganciclovir resistance. Therefore, mRNA was extracted from the tumors formed upon injection of undifferentiated pluripotent cells. From these mRNA preparations, five regions of the TK protein were amplified covering a total of 1162 nucleotides, corresponding to 85% of the total TK sequence (FIG. 7A). The sequenced regions also included the proposed cryptic splice sites (e.g., amplicon 3). The PCR products were directly sequenced (FIG. 7B). The results of this sequencing determined that the all over sequence found in the tumors was identical to the plasmid HSV-TK sequence, suggesting that—if mutations had occurred—they were not representative of the majority of HSV-TK sequences within the tumor. Inspection of the sequencing results did not show any evidence for ambivalent sequencing signals. In addition, the cryptic splice sites described previously were not present in this version of the sequence (neither in the plasmid sequence nor in the tumor-derived sequences); accordingly, no splice variant was detected in the sequencing results.

To investigate whether minority sequences with mutations had occurred within the tumor, two of the PCR amplicons were subcloned and sequenced. No mutation was observed in subclones of amplicon 5; in contrast, in two of the subclones of amplicon 3, there was a single point mutation (FIG. 7C) not located at critical sites of the TK enzyme (ATP and nucleotide-binding sites) (Andrei et al., 2005).

Figure 3A:
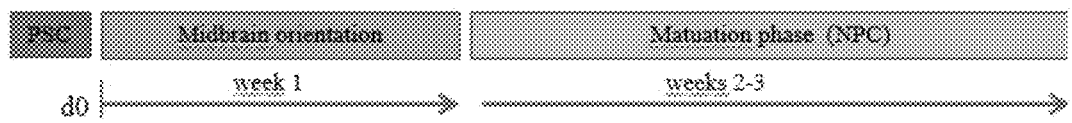
FIGS. 3A-3C: Schedule of cell transplantation and ganciclovir treatment. Different transplantation and ganciclovir treatment protocols were used. (A) Schematic representation of the differentiation protocol towards DA neurons. Pluripotent stem cells were cultured as neurospheres for 1 week for midbrain orientation phase, followed by a 2 or 3 week-maturation phase. (B) Transplantation of undifferentiated pluripotent stem cells with early or late ganciclovir treatment. Early treatment: undifferentiated pluripotent stem cells were transplanted and ganciclovir (or PBS control) was applied by daily intra-peritoneal injection from day 4 to day 19 post-transplantation. Late treatment: undifferentiated pluripotent stem cells were transplanted and ganciclovir (or PBS control) was applied by daily intra-peritoneal injection from day 30 to day 45 post-transplantation. (C) Transplantation of 2 or 3 week NPC: NPC containing—neurospheres were dissociated and transplanted into mice striatum. Ganciclovir (or PBS control) treatment was given from day 4 to day 19 post-transplantation. For all protocols, animals were sacrificed 1 month after termination of ganciclovir treatment.
Figure 3B:
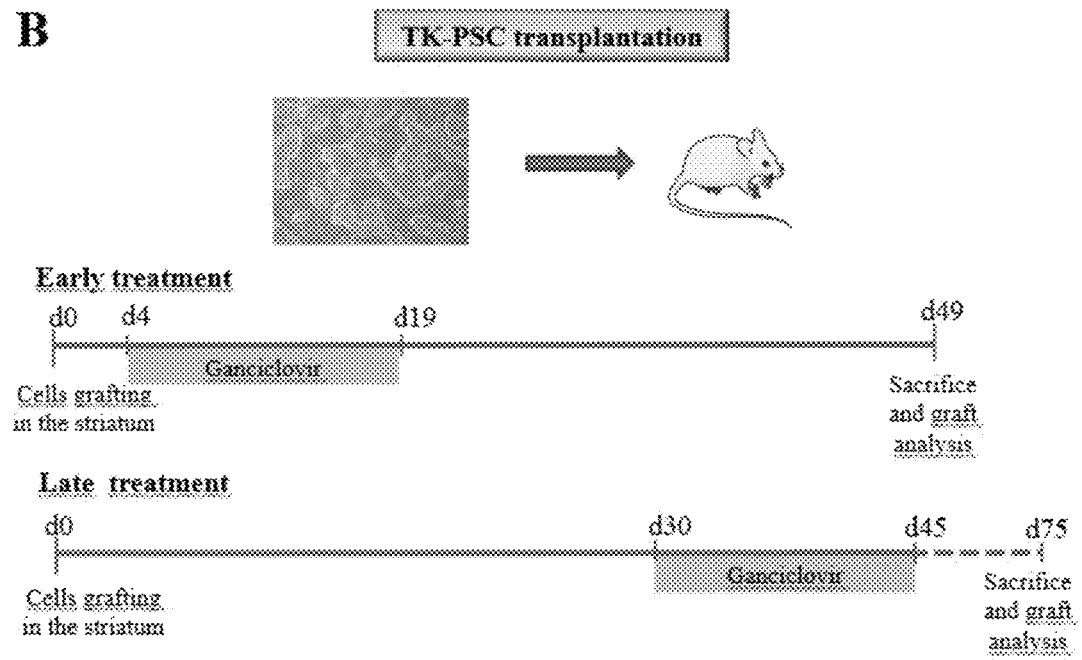
Figure 3C:
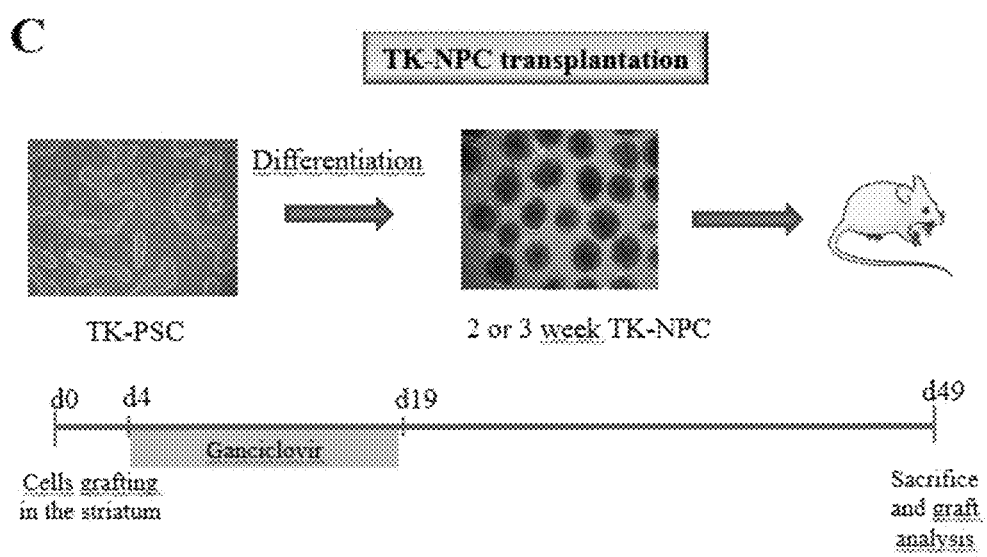
Figures 8A, 8B, 8C, 8D:
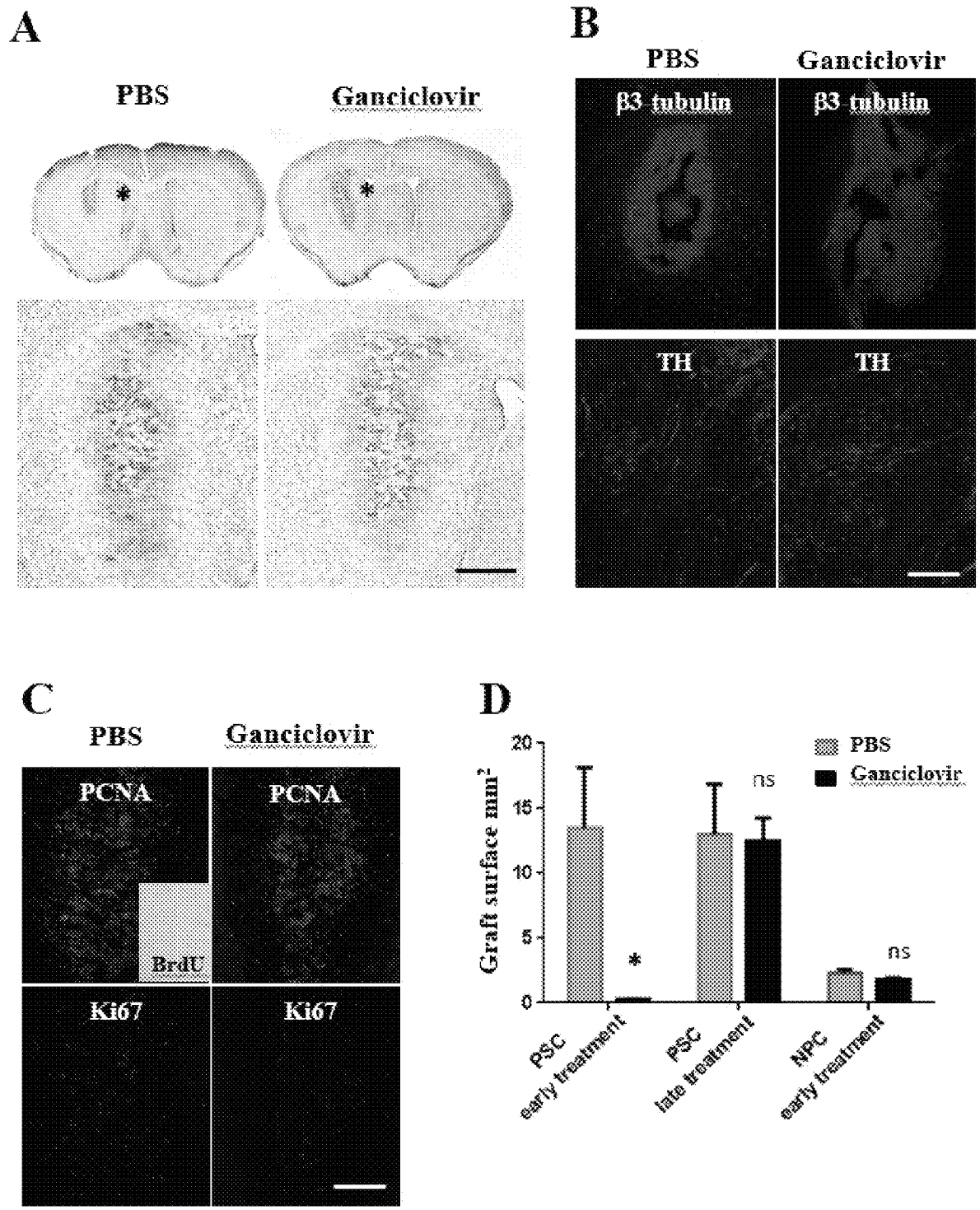
FIGS. 8A-8D: Graft development after transplantation of neural precursor cells (NPC). Mice were transplanted with NPC and treated with PBS or ganciclovir on days 7-22 following transplantation. Mice were sacrificed 4 weeks after the termination of ganciclovir treatment and brains were analyzed. There was no tumor formation, but the grafts had developed into a tissue integrated into the mouse brain. No difference was observed between PBS and ganciclovir treatment (A) cresyl violet coloration. Transplants were strongly positive for beta 3-tubulin (B) upper panel, and weekly positive for TH (B) lower panel. Transplanted cells were PCNA-positive, but Ki67 and BrdU negative (C and insert). (D) Size of transplants under different experimental conditions in the absence (grey histogram) or presence (black histogram) of ganciclovir. Histograms on the left and middle show transplants after injection of pluripotent stem cells (PSC) treated for 2 weeks with ganciclovir 5 days (early treatment) or 30 days after cell transplantation (late treatment). Histograms on the right show transplants after injection of NPC treated with ganciclovir, 5 days after transplantation. Error bars=mean+/−SEM, n=3 to 5 in each group of mice. * p=0,0286 in Mann Whitney test.

Transplantation of TK-NPCs Produced Mature Neurons which were not Sensitive to Ganciclovir Treatment:

The in vivo results, shown so far, were obtained with transplantation of undifferentiated pluripotent stem cells. However, the final goal of neuronal cell therapy is the transplantation of neural precursor cells, which should differentiate into mature neurons and be resistant to ganciclovir treatment. Therefore, 2-3 weeks-NPC containing neurospheres were transplanted (FIGS. 3C, 8). Under these conditions, no tumor formation was observed, even in the absence of ganciclovir treatment (FIG. 8A). In line with these observations, the transplanted cells (assessed by immunofluorescence 7 weeks after transplantation) were abundantly positive for beta 3 tubulin (FIG. 8B, upper panel), while a smaller fraction of cells was TH-positive (FIG. 8B, lower panel). Occasionally nestin-positive cells were observed. None of these markers were affected by ganciclovir treatment.

Markers of cellular proliferation were analyzed by staining of the transplants with antibodies against PCNA and Ki67 (FIG. 8C). Surprisingly, many of the transplanted cells were PCNA positive, while Ki67 staining of the transplants was low to absent. Ganciclovir treatment did not alter this pattern (FIG. 8C, left panels, control and right panels, ganciclovir treatment). To verify whether the PCNA-positive, Ki67-negative cells were proliferating cells, BrdU experiments were performed. No significant BrdU staining was observed (FIG. 8C, insert), suggesting that the absence of Ki67 correctly indicated post-mitotic cells, and that PCNA expression may persist even after proliferation arrest.

To compare tumor formation and response to ganciclovir under different experimental conditions, graft surfaces were quantified (FIG. 8D). When PSCs were transplanted, large tumors (graft surface~10-15 mm2) developed, which was completely prevented by early ganciclovir treatment, while late ganciclovir treatment did not have any effect on tumor size. Finally, upon transplantation of NPC (derived from 2-3 weeks old neurospheres), small non-tumoral transplants (graft surface~2-3 mm) were observed. The size of these transplants was not affected by ganciclovir.

Thus, the present methods provide a novel tool that allows in vivo removal of proliferating, potentially tumorigenic cells from neural transplants. The system is based on the expression of HSV-TK under the control of the cell cycle-dependent Ki67 promoter. It will be particularly useful for the transplantation of pluripotent stem cell-derived neurons. Indeed, HSV-TK expressing cells can be eliminated by treatment of patients with the clinically used, CNS-permeant drug ganciclovir. As the Ki67 promoter will be inactive in mature neurons, treatment with ganciclovir will only eliminate proliferating precursors, but preserve the integrity of differentiated post-mitotic neurons.

Example 2—Materials and Methods

Culture of Undifferentiated Pluripotent Stem Cells:

Human ES cell line HS415 (used from passage 17 to 30, Outi Hovatta, Karolinska Institute, Stockholm, Sweden) was cultured onto human extracellular matrix (MAXGEL® ECM, dilution 1/50 from Sigma or on MATRIGEL™, dilution 1/100, Invitrogen) in a feeder-free culture medium (Nutristem from Biological Industries). Medium was changed one another day to maintain pluripotency. Cells were passaged with enzymatic procedure (ACCUTASE®; Invitrogen) and replated with Rho-associated protein kinase (ROCK) inhibitor (10 µM Y-27632; Ascient Biosciences) during 24h before removal.

Lentiviral Vector Construction, Cell Transduction and Selection:

Construction of plasmids and lentiviral vectors: The final lentivector plasmid was generated by an LR Clonase II (Invitrogen, Carlsbad, Calif.)-mediated recombination of a pENTR plasmid containing the HsKi67 promoter (pENTR-L4-Ki67-L1R), a pENTR plasmid containing the fusion gene TK::Sh, corresponding to the thymidine kinase (TK) gene from Herpes simplex virus type 1 (HSV1) and the Shble gene conferring zeocin resistance, and a pCLX-R4-DEST-R2 lentivector destination cassette.

Lentiviral Vector Production and Titration:

Lentiviral vector stocks were generated using transient transfection of HEK 293T cells with the specific lentivector transfer plasmid, the psPAX2 plasmid encoding gag/pol and the pCAG-VSVG envelope plasmid. Lentivector titer was performed using transduction of HT-1080 cells followed by flow cytometry quantification of GFP-positive cells 5 days after infection. Cell culture: HEK 293T and HT-1080 cells were cultured in high-glucose Dulbecco's modified eagle medium (Sigma) supplemented with 10% fetal calf serum, 1% Penicillin, 1% Streptomycin, and 1% l-glutamine. Transduction of HS415 cell line: 1 up to 5 copies of the lentiviral vector were introduced. HS415 cells were cultured for 5 days before zeocin selection.

Generation of Neurospheres Containing DA Neuropecursors:

NPC were generated as neurospheres to contain DA progenitors as described previously (Tieng et al., 2014). Briefly, neural midbrain orientation is performed during the first week followed by 2 additional weeks of maturation to obtain 1 week or 2 or 3 week-old NPC (FIGS. 1B, 3A).

Generation of NPC in Two Dimensional Culture (2D):

For differentiation in 2D, 3-week old neurospheres were dissociated with ACCUMAX® (Millipore) and replated on polyornithine- (15 µg/mL; Sigma) and laminin- (2 µg/cm$^2$; R&D System) coated cover slips (diameter=0.8 cm) in 24-well plates at 200,000 cells/cm$^2$ in maturation medium for 1 week before analysis by immunofluorescence staining (FIG. 1B).

Flow Cytometry:

Undifferentiated ES cells were enzymatically detached as single cells from human matrix (Accutase, Invitrogen), washed with PBS before a 10 min fixation step in 4% paraformaldehyde (PFA) at room temperature. One week- or 3 week-old neurospheres were dissociated (Accutase, Invitrogen). To detected intracellular antigens, cells were permeabilized in 1× perm/wash buffer (BD bioscience) for 10 min, before 30 min incubation in the dark at room temperature with different antibodies (PE Nanog and PerCp-Cy 5.5 Oct 3/4 from Life Technology, FITC-ki67, rabbit, from Abcam) After washing, cells were immediately run or stored at 4° C. for 24h maximum. For each sample run, 10,000 events were recorded and analyzed. Flow cytometry acquisition was performed using FacsCanto I equipment with 488 and 633 lasers (BD bioscience) and data analysis by Flowjo software.

Immunofluorescence Staining of Fixed Cells:

After 1 week of culture, 2D cultures on cover slips were fixed in 4% PFA for 10 min at room temperature, washed and processed for conventional immunocytochemistry. Paraffin embedded brain was sectioned and processed with cresyl violet for morphological assessment and immunohistochemistry staining. Primary antibody was incubated at 4° C. overnight in agitation in PBS+0.1% triton for cells and 0.3% triton for tissue. Revelation is performed with a secondary antibody at room temperature for 30 min.

Primary antibodies were against Nestin (rabbit polyclonal anti-human, from Chemicon; 1/400), β3-tubulin (mouse monoclonal from Sigma or rabbit polyclonal from Covance; 1/2,000, neuronal nuclei-specific protein (NeuN, mouse monoclonal from Chemicon; 1/1,000), glial fibrillary acidic protein (GFAP, rabbit polyclonal from Dako; 1/2,000), proliferating cell nuclear antigen (PCNA, mouse monoclonal from Dako; 1/100), tyrosine hydroxylase (TH; rabbit polyclonal from Millipore; 1/500). Detection of primary antibodies was performed using appropriate species-specific Alexa 488- or Alexa 555-labeled secondary antibodies. Controls included examination of the cell or tissue autofluorescence and omission of the first antibody. Cell nuclei were stained with DAPI. Sections and cell cultures were mounted in Fluorosave (Calbiochem) or Eukitt (Kindler GmbH) and observed with an Axioscop 2 plus microscope equipped with appropriate filters, Axiocam color camera, and Axiovision software (Leitz).

Cell Proliferation Measurement by Calcein Assay:

Cells were plated onto a 96 wells pre-coated with poly-ornothine+ECM (1/50). Respectively 1000 cells for pluripotent stem cells, 5000 cells for early NPC and 30000 cells for late NPC. Ganciclovir (Cemevene diluted in PBS, Roche) treatment was added the day after cell plating for PSC, 3 days later for early NPC and one week later for late NPC. Calcein (2 µM) was added for different time course of ganciclovir treatment (24H to 96H). Cell survival was measured by calcein integration after 24h of incubation in a 37° C. incubator.

Stereotaxic engraftment and ganciclovir treatment:

Undifferentiated pluripotent stem cells (20000 cells/µL) and dissociated neurospheres (100.000 cells/µL) were injected in the striatum of anesthetized mice using a 27-G Hamilton syringe. Injection coordinates for lateral striatum were: bregma=0.74 mm, mediolateral=2.25 mm, dorsoventral=3.5 mm; for medial striatum: bregma=0.74 mm, mediolateral=1.4 mm, dorsoventral=2.8 mm. Mice were euthanized one month later after ganciclovir termination.

Morphological and Phenotypic Analysis of Injected Surviving Cells:

Anesthetized mice were fixed by intracardiac perfusion of 4% paraformaldehyde in phosphate-buffered saline. Immunohistochemical detection was performed on 10-µm thick free-floating cryostat sections using Alexa 488-, or 555-labeled secondary antibodies or the biotin-avidin-peroxidase complex method (Vector). The following primary antibodies were used: Nestin (rabbit polyclonal anti-human, from Chemicon, 1/400), β3-tubulin (mouse monoclonal from Sigma or rabbit polyclonal from Covance, 1/2000), Neuronal Nuclei-specific protein (NeuN, mouse monoclonal from Chemicon, 1/1000), Glial Fibrillary Acidic Protein (GFAP, rabbit polyclonal from Dako, 1/2000), Proliferating Cell Nuclear Antigen (PCNA, mouse monoclonal from Dako, 1/100), Tyrosine Hydroxylase (TH, rabbit polyclonal from millipore, 1/500), iba 1 (polyclonal rabbit from Wako, 1/500), HSV-TK (mouse monoclonal, Gentaur, 1/100), ki67 (monoclonal rabbit, Abcam, 1/100 or mouse, Chemicon, 1/100). CD31 (Detection of primary antibodies was performed using appropriate species specific Alexa 488- or Alexa 555-labeled secondary antibodies. Controls included examination of the cell or tissue auto-fluorescence and omission of the first antibody. Cell nuclei were stained with DAPI. Sections and cells cultures were mounted in Fluorosave (Calbiochem) or Eukitt (Kindler GmbH, Germany) and observed with an Axioscop2 plus microscope equipped with appropriate filters, Axiocam color camera and Axiovision software (Leitz, Germany). Confocal imaging was achieved with an LSM 510 Meta confocal laser scanner and Bitplane SS Imaris 5.7.2 software.

BrdU Labelling:

BrdU (100 mg/kg, Millipore) was injected intraperitoneally twice daily for 3 consecutive days. Mice were sacrificed 5 days later and perfused, through the heart, with PBS and 4% paraformaldehyde in PBS. Brain and small intestine were embedded in paraffin and 10 mm thick frontal section were processed for BrdU immunohistochemiscal detection using a BrdU Immunohistochemistry Kit (Chemicon, Cat No. 2760), small intestine section serving as control.

Thymidine Kinase Sequencing:

Total RNA was extracted and purified according the manufacturers' instructions (high pure FFPE RNA micro kit, Roche) from PFA-fixed, paraffin-embedded tissue delimited to teratoma area induced by PSC transplantation and late ganciclovir treatment (IG. 7). Typically, RNA isolated from formalin-fixed tissue is fragmented and the bulk of RNA obtained is around 200 bases in length. After DNase treatment, CDNA synthesis is performed from RNA pool extracted (Takara). Thymidine kinase gene expressed inside the teratoma was amplified by using a set of different overlapping primers along the thymidine sequence (1162 bp). PCR reaction is performed with a proofreading taq polymerase (Q5 high fidelity, NEB) during 35 cycles with 30" at 95° C., 30" at 58° C. and 1 min at 72° C. Primers for fragment 1 are for forward F 5'-GAG CGGTGGTTCGACAAGTGG-3' (SEQ ID NO: 1) and reverse R 5'-CCTCAGCAGGGTTGGCATC-3' (SEQ ID NO: 2), fragment 2, F 5'-GATGCCAACCCTGCTGAGG-3' (SEQ ID NO: 3) and R 5'-GTCCAGCCTGTGCTGGGTG-3' (SEQ ID NO: 4), fragment 3, F 5'-CACCCAGCACAGGCTGGAC-3' (SEQ ID NO: 5) and R 5'-CAGGGCCACAAAAGCCAGCAC-3' (SEQ ID NO: 6), fragment 4, F 5'-GTGCTGGCTTTTGTGGCCCTG-3' (SEQ ID NO: 7) and R 5'-CCAGAGAGCTGTCCCCAGTC-3' (SEQ ID NO: 8), fragment 5, F 5'-GTCCCCTGCTGGATGCAGAG-3' (SEQ ID NO: 9) and R 5'-CTC TGC ATCCAGCAGGGGAC-3' (SEQ ID NO: 10). Fragment 1 to 5 were directly sequenced or subcloned into topo TA cloning kit (Invitrogen) before performing sequencing of the different bacterial clones (Microsynth, AG).

Example 3—Suicide Gene Construct Characterization

Figure 9:
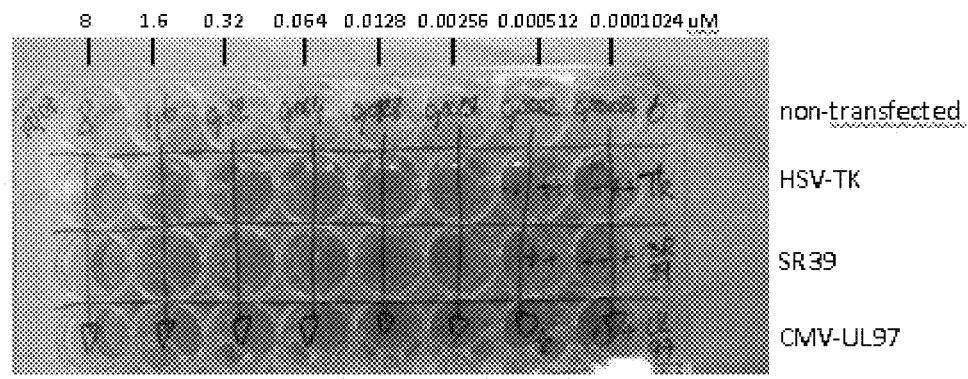
FIG. 9: Image of plate in cell viability assay. Cells were transfected with a construct expressing HSV-TK, SR39, or CMV-UL97.

In further experiments, cell proliferation assay was performed using different suicide gene constructs in combination with various drugs, such as acyclovir, ganciclovir, or pencilovir. In the first assay, a kinase from human cytomegalovirus (CMV), UL97, was used as a novel suicide gene. The HEK cells were transfected with a high copy number of the respective plasmids. It was observed that UL97 under the UBI promoter plasmid when transfected in the HEK cells showed sensitivity to ganciclovir (FIG. 9) similar to the HSV-TK and SR39 plasmids.

Figure 10A:
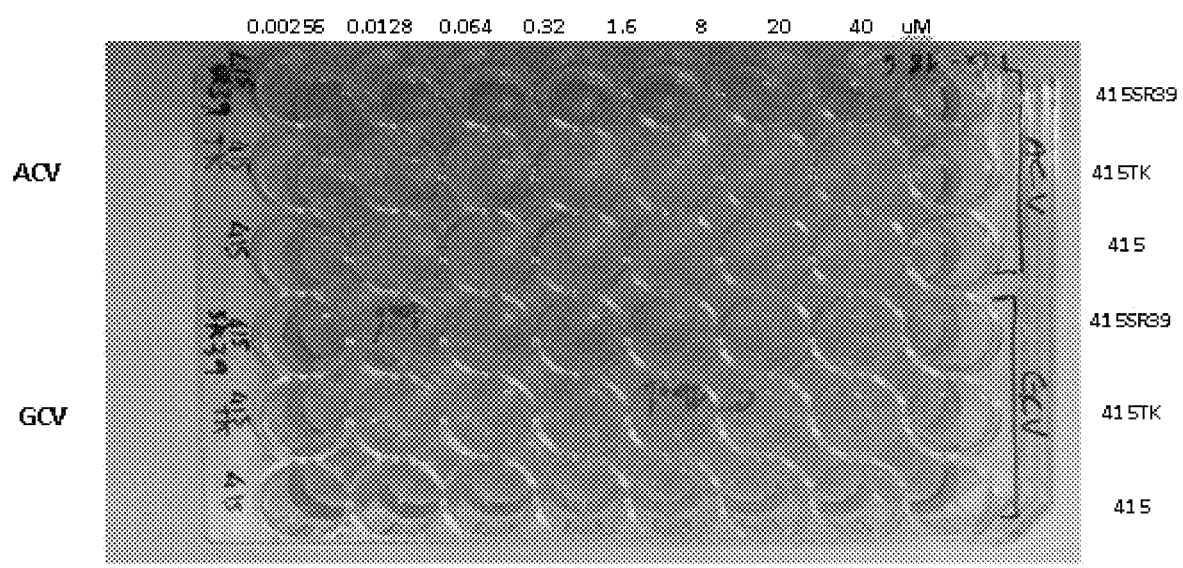
FIGS. 10A-10B: (A) Cell viability assay with cells transfected with HSV-TK or SR39. Cells were treated with acyclovir or ganciclovir. (B) Cell viability assay with cells transfected with HSV-TK or SR39 and treated with penciclovir.

In another experiment, the cells were transduced with a low copy number of the plasmids and, thus, differences between the different nucleoside analogs could be observed. It was observed that ganciclovir killed HSV-TK and SR39-transduced cells at a relatively low concentration, while very high concentrations of acyclovir are needed (FIG. 10A). Ganciclovir at high concentrations is also toxic to non-transduced cells.

Figure 10B:
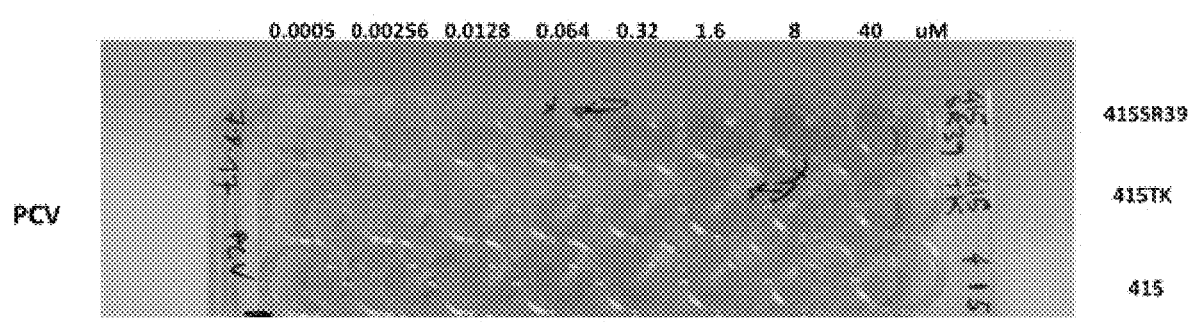

Finally, the cell proliferation assay was also performed with the SR39 or HSV-TK-transduced cells treated with penciclovir. It was found that penciclovir kills the transduced cells at relatively low concentrations and did not show any toxicity in untransduced cells (FIG. 10B). Thus, penciclovir may be used as the prodrug with the suicide gene construct, such as HSV-TK, SR39, or UL97.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

Alisky and Davidson, Hum. Gene Ther. 77:2315-2329, 2000.
Amit et al., Dev. Bio., 227:271-278, 2000.
Andrei G, et al., Journal of virology 79: 5863-5869, 2005.
Balciunaite et al., Molecular and Cellular Biology 25(18), 2005.
Blomer et al., J. Virol., 71(9):6641-6649, 1997.
Bray et al., PNAS USA 91, 1256-1260, 1994.
Byrne et al., Nature, 450(7169):497-502, 2007.
Challita, P. M. and Kohn, D. B., Proc. Natl. Acad. Sci. USA 91: 2567, 1994.
Chalmers D et al., Molecular therapy: the journal of the American Society of Gene Therapy 4: 146-148, 2001.
Chang et al., PLOS One 8(4):e61196, 2013.
Chang, et al., J. Virology 67, 743-752, 1993.
Chen et al., Nature Methods, 8:424-429, 2011.
Chu et al., Gene 13: 197, 1981.
Couch et al., Am. Rev. Resp. Dis., 88:394-403, 1963.
Daly et al., Nature 342:816-819, 1989.
Davidson et al., Nat. Genet. 3:219-223, 1993.
Davidson et al., PNAS 97:3428-3432, 2000.
Davis et al., Basic Methods in Molecular Biology, Elsevier, 1986.
Denny et al., Biomedicine Biotechnol. 1:48-70, 2003
Dimova et al., Oncogene 24:2810-2826, 2005.
Finer, et al., Blood 83, 43-50, 1994.
Fischer et al., Nucleic Acids Research 2015.
Froehler et al., Nucleic Acids Res., 14(13):5399-5407, 1986.
Ganat et al., J. Clin. Invest., 122:2928-2939, 2012.
Gill et al., Molecular and Cellular Biology 33(3):498-513, 2013.
Graham and Prevec, Biotechnology, 20:363-390, 1992.
Graham et al, J. General Virology, 36:59-74, 1977.
Graham et al., Virology, 52:456, 1973.
Grant et al., Molecular Biology of the Cell 24(23):3634-3650, 2013.
Grunhaus and Horwitz, Seminar in Virology, 3:237-252, 1992.
Huang et al., J. Virology 65:3193-3199, 1994.
Huang et al., Mol Cell. Biol. 73:7476-7486, 1993.
Imaki et al., Cancer Res. 63(15):4607-13, 2003.
International Publication No. PCT/JP2009/062911
International Publication No. PCT/JP2011/069588
International Publication No. WO 02/101057
International Publication No. WO 2007/069666
International Publication No. WO 95/30763
Kang et al., Biochem Biophys Res Commun. 420(4):822-7, 2012.
Kotini A G, et al., Molecular therapy Nucleic acids 5: e284, 2016.
Kriks et al., Nature, 480:547-551, 2011.
Kunkle, PNAS 52:488, 1985.
Levin et al., Gene 108:167-174, 1991.
Llano et al., Genes Dev. 22(17):2400-13, 2008.
Ludwig et al., Nat. Biotechnol., 24(2):185-187, 2006b.
Ludwig et al., Nat. Methods, 3(8):637-46, 2006a.
Macejak and Sarnow, Nature, 353:90-94, 1991.
Mjelle et al., DNA Repair 30:53-67, 2015.
Muller et al., Nucleic Acids Res. 40(4):1561-1578, 2012.
Naldini et al., Science, 272(5259):263-267, 1996.
Pawar et al. Oncogene 23(36):6125-35, 2004.
Pelletier and Sonenberg, Nature, 334(6180):320-325, 1988.
Ren et al., Genes and Dev. 16:245-256, 2002.
Renan, Radiother. Oncol., 19:197-218, 1990.
Reubinoff et al., Nat. Biotechnol., 18:399-404, 2000.
Robinson, et al., Gene Therapy 2, 269-278, 1995.
Salvatore et al., Cancer Res. 67(21):10148-10158, 2007.
Sambrook et al., Molecular Cloning, a laboratory manual, Cold Spring Harbor Laboratories, New York, 1989.
Seguin et al., Molecular and Cellular Biology 29(2), 2009.
Stein et al., J Virol 73:3424-3429, 1999.
Suzuki et al., Nature Cell Biology 18:382-392, 2016.
Takahashi et al., Cell, 126(4):663-76, 2007.
Thomson and Marshall, Curr. Top. Dev. Biol., 38:133-165, 1998.
Thomson and Odorico, Trends Biotechnol., 18(2):53-57, 2000.
Tieng V, et al., Stem cells and development 23(13):1535-1547, 2014.
Top et al., J. Infect. Dis., 124:155-160, 1971.
U.S. Pat. No. 4,682,195
U.S. Pat. No. 4,683,202
U.S. Pat. No. 5,591,624
U.S. Pat. No. 5,645,897
U.S. Pat. No. 5,705,629
U.S. Pat. No. 5,843,780
U.S. Pat. No. 5,925,565
U.S. Pat. No. 5,928,906
U.S. Pat. No. 5,935,819
U.S. Pat. No. 5,980,885
U.S. Pat. No. 5,994,136
U.S. Pat. No. 6,013,516
U.S. Pat. No. 6,013,517
U.S. Pat. No. 6,103,470
U.S. Pat. No. 6,200,806
U.S. Pat. No. 6,416,998

U.S. Pat. No. 6,740,320
U.S. Pat. No. 7,029,913
U.S. Pat. No. 7,442,548
U.S. Pat. No. 7,598,364
U.S. Pat. No. 7,968,337
U.S. Pat. No. 7,989,425
U.S. Pat. No. 8,058,065
U.S. Pat. No. 8,071,369
U.S. Pat. No. 8,093,053
U.S. Pat. No. 8,129,187
U.S. Pat. No. 8,178,349
U.S. Pat. No. 8,183,038
U.S. Pat. No. 8,268,620
U.S. Pat. No. 8,546,140
U.S. Pat. No. 8,691,574
U.S. Pat. No. 8,741,648
U.S. Pat. No. 8,900,871
U.S. Pat. No. 9,175,268
U.S. Patent Publication No. 2003/0211603
U.S. Patent Publication No. 2009/0246875
U.S. Patent Publication No. 2010/0210014
U.S. Patent Publication No. 2010/0323444
U.S. Patent Publication No. 20120276636
U.S. Patent Publication No. 2014/0315304
Wernig et al., *Proc. Natl. Acad. Sci. USA.*, 105:5856-5861, 2008.
Westendorp et al., *Nucleic Acids Research* 1-13, 2011.
Whitfield et al., *Nature Reviews Cancer* 6:99-106, 2006.
Wu et al., *J Biol Chem.* 3(43):29396-29404, 2008.
Wu X. and Lee H. *Oncogene* 21(51): 7786-96, 2002.
Xu et al., *Nat. Biotechnol.*, 19:971-974, 2001.
Yamamoto et al., *Nucleic Acid Res.* 2016.
Yamanaka et al., *Cell,* 131(5):861-72, 2007.
Ying et al., *Cell,* 115:281-292, 2003.
Yu et al., *Science,* 318:1917-1920, 2007.
Zambon A. C. *Cytometry A.* 77(6):564-570, 2010.
Zapp et al., *Nature* 342:714-716, 1989.
Zhang et al., *Molecular Cancer* 8(11), 2009.
Zufferey et al., *Nat. Biotechnol.,* 15(9):871-875, 1997.

What is claimed is:

1. An in vitro cell composition comprising precursor cells that are not pluripotent stem cells, the precursor cells comprise expression vectors encoding a cell cycle-dependent promoter operably linked to a suicide gene coding sequence, wherein the suicide gene is cytomegalovirus (CMV) UL97 gene or a mutant herpes simplex virus thymidine kinase (HSV-TK).

2. The cell composition of claim 1, wherein the precursor cells are further defined as neural precursor cells, cardiomyocyte precursor cells, endothelial precursor cells, pancreatic precursor cells, kidney precursor cells, oligodendrocyte precursor cells, hematopoietic precursor cells, myeloid precursor cells, mesenchymal precursor cells, retinal precursor cells, or osteoclast precursor cells.

3. The cell composition of claim 1, wherein the precursor cells are further defined as a neural precursor cells.

4. The cell composition of claim 1, wherein the precursor cells are derived from induce pluripotent stem cells (iPSC).

5. The cell composition of claim 3, wherein the neural precursor cells are further defined as expressing at least one of the markers selected from the group consisting of musashi, nestin, sox2, vimentin, pax6, and sox1.

6. The cell composition of claim 1, wherein the expression vectors are integrated into chromosomes of the precursor cells.

7. The cell composition of claim 1, wherein the expression vectors are chromosomally integrating vectors.

8. The cell composition of claim 7, wherein the expression vectors are lentiviral vectors.

9. The cell composition of claim 1, wherein the CMV-UL97 is mutant CMV-UL97.

10. The cell composition of claim 1, wherein the mutant HSV-TK is SR11, SR26, SR39, SR4, SR15, SR32, or SR53.

11. The cell composition of claim 1 wherein the cell cycle-dependent promoter is a Ki-67, PCNA, CCNA2, CCNB2, DLGAP5, or TOP2A promoter.

12. The cell composition of claim 1, wherein the cell cycle-dependent promoter is a synthetic cell cycle promoter.

13. The cell composition of claim 1, wherein the expression vectors further encode a selectable marker.

14. The cell composition of claim 13, wherein the selectable marker is encoded by an antibiotic resistance gene or a gene encoding a fluorescent protein.

15. The cell composition of claim 1, wherein the expression vectors are viral vectors.

16. The cell composition of claim 15, wherein the viral vectors are lentiviral vectors, adenoviral vectors, retroviral vectors, vaccina viral vectors, adeno-associated viral vectors, herpes viral vectors, or polyoma viral vectors.

* * * * *